US009566123B2

(12) United States Patent
Daon

(10) Patent No.: US 9,566,123 B2
(45) Date of Patent: Feb. 14, 2017

(54) SURGICAL LOCATION MONITORING SYSTEM AND METHOD

(71) Applicant: Ehud (Udi) Daon, North Vancouver (CA)

(72) Inventor: Ehud (Udi) Daon, North Vancouver (CA)

(73) Assignee: Navigate Surgical Technologies, Inc., Vancouver, BC (CA)

( * ) Notice: Subject to any disclaimer, the term of this patent is extended or adjusted under 35 U.S.C. 154(b) by 178 days.

(21) Appl. No.: 14/598,484

(22) Filed: Jan. 16, 2015

(65) Prior Publication Data

US 2015/0147714 A1  May 28, 2015

Related U.S. Application Data

(63) Continuation-in-part of application No. 13/571,284, filed on Aug. 9, 2012, now Pat. No. 8,938,282, and a
(Continued)

(51) Int. Cl.
*A61B 5/055* (2006.01)
*A61B 19/00* (2006.01)
(Continued)

(52) U.S. Cl.
CPC ............ *A61B 19/54* (2013.01); *A61B 5/055* (2013.01); *A61B 5/06* (2013.01); *A61B 6/032* (2013.01);
(Continued)

(58) Field of Classification Search
CPC . A61B 10/0233; A61B 17/3211; A61B 19/54; A61B 1/00; A61B 1/24; A61B 2017/00477; A61B 2090/3925; A61B 2090/3954; A61B 2090/3966; A61B 2090/3983; A61B 2090/3991; A61B 34/20; A61B 5/055; A61B 5/06; A61B 5/062; A61B 5/064; A61B 5/72; A61B 6/032; A61B 6/12; A61B 6/14; A61B 6/145; A61B 6/52; A61B 8/0841; A61B 90/16; A61B 90/39; A61C 19/04; A61C 1/0007; A61C 1/082; A61C 3/02
See application file for complete search history.

(56) References Cited

U.S. PATENT DOCUMENTS 5,230,623 A   7/1993 Guthrie
5,438,991 A   8/1995 Yu et al.
(Continued)

FOREIGN PATENT DOCUMENTS

DE   10 2005 026654   12/2006
DE      102009009158    9/2010
(Continued)

OTHER PUBLICATIONS

European Patent Office, International Written Opinion, dated Sep. 29, 2014 (PCT/IB2014/060403).
(Continued)

*Primary Examiner* — Mark Remaly
(74) *Attorney, Agent, or Firm* — Kevin R. Erdman; Brannon Sowers & Cracraft PC

(57) ABSTRACT

A position monitoring system comprises a single composite fiducial reference comprised of a fiducial key and a fiducial extension rigidly and removably attached to the fiducial key, a tracker for obtaining image information of the surgical site, and a computer system with processor, memory, a software program, and access to a database. The computer has scan data of an area of a surgical patient with the fiducial reference fixed to the area by a multipodal surgical screw fixture. A uniquely identifiable first marker is attached to the fiducial key in a predetermined fixed relative position and orientation. The computer determines the relative position and orientation of the marker based on live image informa-
(Continued)

tion from the tracker, relates and displays the current position and orientation of the composite fiducial reference to the scan data during a surgical procedure. Further implements at the surgical site may bear further markers that may be tracked. The marker may also serve as fiducial extension, to which end it may be uniquely shaped or marked.

47 Claims, 14 Drawing Sheets

Related U.S. Application Data continuation-in-part of application No. 13/822,358, filed on Mar. 12, 2013.

(60) Provisional application No. 61/553,058, filed on Oct. 28, 2011, provisional application No. 61/616,718, filed on Mar. 28, 2012.

(51) Int. Cl.
| | |
|---|---|
| A61B 6/03 | (2006.01) |
| A61C 1/08 | (2006.01) |
| A61B 5/06 | (2006.01) |
| A61B 6/12 | (2006.01) |
| A61B 6/14 | (2006.01) |
| A61B 8/08 | (2006.01) |
| A61B 10/02 | (2006.01) |
| A61C 1/00 | (2006.01) |
| A61B 17/00 | (2006.01) |

(52) U.S. Cl.
CPC ............... *A61B 6/12* (2013.01); *A61B 34/20* (2016.02); *A61B 90/16* (2016.02); *A61B 90/39* (2016.02); *A61C 1/082* (2013.01); *A61B 6/14* (2013.01); *A61B 8/0841* (2013.01); *A61B 10/0233* (2013.01); *A61B 2017/00477* (2013.01); *A61B 2090/3925* (2016.02); *A61B 2090/3937* (2016.02); *A61B 2090/3954* (2016.02); *A61B 2090/3966* (2016.02); *A61B 2090/3983* (2016.02); *A61B 2090/3991* (2016.02); *A61C 1/0007* (2013.01)

(56) References Cited

U.S. PATENT DOCUMENTS

| | | |
|---|---|---|
| 5,603,318 A | 2/1997 | Heilbrun et al. |
| 5,828,770 A | 10/1998 | Leis et al. |
| 5,967,777 A | 10/1999 | Klein |
| 6,122,541 A | 9/2000 | Cosman et al. |
| 6,468,265 B1 | 10/2002 | Evans et al. |
| 6,529,765 B1 | 3/2003 | Franck et al. |
| 7,653,455 B2 | 1/2010 | Cinador |
| 7,720,521 B2 | 5/2010 | Chang |
| 7,758,345 B1 | 7/2010 | Christensen |
| 7,894,878 B2 | 2/2011 | Noujeim |
| 7,899,512 B2 | 3/2011 | Labadie |
| 8,172,573 B2 | 5/2012 | Sonenfeld |
| 2004/0002642 A1 | 1/2004 | Dekel et al. |
| 2004/0097952 A1 | 5/2004 | Sarin et al. |
| 2004/0138556 A1 | 7/2004 | Cosman |
| 2005/0085719 A1 | 4/2005 | Franklin et al. |
| 2005/0163342 A1 | 7/2005 | Persky |
| 2005/0182318 A1 | 8/2005 | Kaji et al. |
| 2006/0142657 A1 | 6/2006 | Quaid et al. |
| 2006/0165310 A1 | 7/2006 | Mack |
| 2006/0212044 A1 | 9/2006 | Bova et al. |
| 2006/0247517 A1 | 11/2006 | Labadie et al. |
| 2006/0281991 A1 | 12/2006 | Fitzpatrick |
| 2007/0208252 A1 | 9/2007 | Makower |
| 2007/0223910 A1 | 9/2007 | Aoki |
| 2007/0253541 A1 | 11/2007 | Sukovic et al. |
| 2008/0026338 A1 | 1/2008 | Cinader |
| 2008/0161682 A1 | 7/2008 | Kendrick et al. |
| 2008/0171305 A1 | 7/2008 | Sonenfeld et al. |
| 2008/0183071 A1 | 7/2008 | Strommer |
| 2008/0193896 A1 | 8/2008 | Yang |
| 2008/0200927 A1 | 8/2008 | Hartmann et al. |
| 2008/0262345 A1 | 10/2008 | Fichtinger |
| 2008/0319491 A1 | 12/2008 | Schoenefeld |
| 2009/0012509 A1 | 1/2009 | Csavoy |
| 2009/0171196 A1 | 7/2009 | Olson et al. |
| 2009/0253095 A1 | 10/2009 | Salcedo |
| 2010/0039506 A1 | 2/2010 | Sarvestani et al. |
| 2010/0049195 A1 | 2/2010 | Park et al. |
| 2010/0168562 A1 | 7/2010 | Zhao et al. |
| 2010/0168763 A1 | 7/2010 | Zhao et al. |
| 2010/0210939 A1 | 8/2010 | Hartmann et al. |
| 2010/0217139 A1 | 8/2010 | Pinter et al. |
| 2011/0008751 A1 | 1/2011 | Patterssen |
| 2011/0087332 A1 | 4/2011 | Bojarski et al. |
| 2011/0217667 A1 | 9/2011 | Groscruth |
| 2011/0257653 A1 | 10/2011 | Hughes |
| 2012/0065496 A1 | 3/2012 | Stratton |
| 2012/0115107 A1 | 5/2012 | Adams |
| 2012/0259204 A1 | 10/2012 | Carrat et al. |
| 2012/0283637 A1 | 11/2012 | Cohen |
| 2013/0063558 A1 | 3/2013 | Phipps |
| 2013/0258353 A1 | 10/2013 | Kosmecki et al. |
| 2013/0322719 A1 | 12/2013 | Dekel et al. |
| 2014/0030669 A1 | 1/2014 | Hey et al. |
| 2014/0049629 A1 | 2/2014 | Siewerdsen et al. |

FOREIGN PATENT DOCUMENTS

| | | |
|---|---|---|
| DE | 2010042540 | 4/2012 |
| DE | 10 2011 012 460.8 | 8/2012 |
| EP | 1527417 | 9/2011 |
| FR | 2 929 794 | 10/2009 |
| GB | 2 416 949 | 2/2006 |
| JP | 2000046546 | 2/2000 |
| JP | 2007253748 | 10/2007 |
| JP | 2009172411 | 5/2009 |
| WO | 99/27839 | 6/1999 |
| WO | 02/076302 | 10/2002 |
| WO | 2008/009136 | 1/2008 |
| WO | 2010/086374 | 5/2010 |
| WO | 2001/113441 | 9/2011 |
| WO | 2012/068679 | 5/2012 |
| WO | 2012068679 | 5/2012 |
| WO | 2012095642 | 7/2012 |
| WO | 2012/149548 | 11/2012 |
| WO | 2012149548 | 11/2012 |
| WO | WO2012149548 | 11/2012 |
| WO | 2013096766 | 6/2013 |
| WO | 2011/109041 | 10/2013 |
| WO | 2013144208 | 10/2013 |

OTHER PUBLICATIONS

European Patent Office, International Written Opinion, dated Oct. 17, 2014 (PCT/EP2014/067280).
European Patent Office, International Search Report, dated Jul. 17, 2014 (PCT/EP2014/058406).
European Patent Office, International Written Opinion, dated Aug. 18, 2014 (PCT/EP2014/058406).
European Patent Office, International Written Opinion, dated Jul. 30, 2014 (PCT/EP2014/057656).
European Patent Office, International Written Opinion, dated Jul. 30, 2014 (PCT/EP2014/060018).
EPO, International Search Report and Written Opinion for PCT/EP2013/073401, Mar. 7, 2014.
International Searching Authority, International Search Report, dated Sep. 3, 2013 (PCT/IL2013/000032).
International Searching Authority, International Written Opinion, dated Sep. 3, 2013 (PCT/IL2013/000032).
International Searching Authority, International Search Report, dated Sep. 16, 2013 (PCT/EP2013/056525).

(56) References Cited

OTHER PUBLICATIONS

International Searching Authority, International Search Report, mailed Sep. 17, 2013 (PCT/IL2013/000031).
Prosecution of U.S. Appl. No. 13/571,284, from First Office Action of Aug. 15, 2013 to Amendment with Request for Continued Examination of Feb. 26, 2014.
International Searching Authority, International Search Report, mailed Mar. 4, 2013 (PCT/IL2012/000363).
International Searching Authority, International Written Opinion, mailed Mar. 4, 2013 (PCT/IL2012/000363).
International Searching Authority, International Search Report, dated Feb. 18, 2014 (PCT/EP2013/073416).
International Searching Authority, International Written Opinion, dated Feb. 18, 2014 (PCT/EP2013/073416).
European Patent Office, International Search Report, International Application No. PCT/EP2013/073401, dated Mar. 19, 2014.
European Patent Office, Written Opinion of the International Searching Authority, International Application No. PCT/EP2013/073401, dated Mar. 19, 2014.
European Patent Office, International Search Report, International Application No. PCT/EP2014/057656, dated Aug. 11, 2014.
European Patent Office, Written Opinion of the International Searching Authority, International Application No. PCT/EP2014/051656, dated Aug. 11, 2014.
European Patent Office, International Search Report, International Application No. PCT/EP2014/060018, dated Aug. 11, 2014.
European Patent Office, Written Opinion of the International Searching Authority, International Application No. PCT/EP2014/060018, dated Aug. 11, 2014.
Prosecution of U.S. Appl. No. 13/713,165, First Office Action of Aug. 13, 2014 and Amendment of Aug. 14, 2014.
Japanese Patent Office (JPO) Notice of Preliminary Rejection,Japan Patent Application No. 2014-537811, Based upon PCT/IL2012/000363, Jan. 25, 2016, which claims priority to U.S. Appl. No. 13/571,284, now U.S. Pat. No. 8,938,282.
Japanese Patent Office (JPO) Notice of Preliminary Rejection,Japanese Patent Application No. 2015-541159, Based upon PCT/EP2013/0073401, Mar. 1, 2016, which claims priority to U.S. Appl. No. 14/562,691, now U.S. Pat. No. 8,908,918.
European Patent Office, Written Opinion of the International Searching Authority, International Application No. PCT/IL2015/050400, Navigate Surgical Technologies, Inc., Jul. 16, 2015.
European Patent Office, International Search Report, International Application No. PCT/IL2015/050400, Navigate Surgical Technologies, Inc., Jul. 16, 2015.
USPTO, Non-Final Office Action for U.S. Appl. No. 13/744,967, dated Jun. 30, 2015.
USPTO, Non-Final Office Action for U.S. Appl. No. 13/745,249, dated Jun. 30, 2015.
USPTO, Final Office Action for U.S. Appl. No. 13/745,763, dated Jul. 8, 2015.
Arizona Center for Laser Dentistry, Root Canals at the Arizona Center for Laser Dentistry, Captured via web.archive.org on Dec. 19, 2010, retrieved Jun. 2, 2015.
USPTO, Non- Final Office Action for U.S. Appl. No. 13/822,358, dated Feb. 13, 2015.
USPTO, Response to Non-Final Office Action for U.S. Appl. No. 13/745,763, dated Mar. 25, 2015.

SURGICAL LOCATION MONITORING SYSTEM AND METHOD

CROSS REFERENCE TO RELATED APPLICATIONS

The present application is a continuation-in-part of PCT International Application Serial Number PCT/IL2012/000363, filed Oct. 23, 2013, and a continuation-in part of U.S. patent application Ser. No. 13/571,284, filed Oct. 28, 2011, both of which claim priority under 35 U.S.C. §119(e) of U.S. Patent Provisional Application Ser. Nos. 61/553,058, filed on Oct. 28, 2011, and 61/616,718, filed Mar. 28, 2012, the disclosures of which are incorporated by reference herein. The present application also claims priority under 35 U.S.C. §120 of U.S. patent application Ser. No. 13/822,358, filed Mar. 12, 2013.

BACKGROUND OF THE INVENTION

Field of the Invention

The invention relates to location monitoring hardware and software systems. More specifically, the field of the invention is that of surgical equipment and software for monitoring surgical conditions.

Description of the Related Art

Visual and other sensory systems are known, with such systems being capable of both observing and monitoring surgical procedures. With such observation and monitoring systems, computer aided surgeries are now possible, and in fact are being routinely performed. In such procedures, the computer software interacts with both clinical images of the patient and observed surgical images from the current surgical procedure to provide guidance to the physician in conducting the surgery. For example, in one known system a carrier assembly bears at least one fiducial marker onto an attachment element in a precisely repeatable position with respect to a patient's jaw bone, employing the carrier assembly for providing registration between the fiducial marker and the patient's jaw bone and implanting the tooth implant by employing a tracking system which uses the registration to guide a drilling assembly. With this relatively new computer implemented technology, further improvements may further advance the effectiveness of surgical procedures.

SUMMARY OF THE INVENTION

The present invention is a surgical hardware and software monitoring system and method which allows for surgical planning while the patient is available for surgery, for example while the patient is being prepared for surgery so that the system may model the surgical site. In one embodiment, the model may be used to track contemplated surgical procedures and warn the physician regarding possible boundary violations that would indicate an inappropriate location in a surgical procedure. In another embodiment, the hardware may track the movement of instruments during the procedure and in reference to the model to enhance observation of the procedure. In this way, physicians are provided an additional tool to improve surgical planning and performance.

The system uses a particularly configured fiducial reference, to orient the monitoring system with regard to the critical area. The fiducial reference is attached to a location near the intended surgical area. For example, in the example of a dental surgery, a splint may be used to securely locate the fiducial reference near the surgical area. The fiducial reference may then be used as a point of reference, or a fiducial, for the further image processing of the surgical site. The fiducial reference may be identified relative to other portions of the surgical area by having a recognizable fiducial marker apparent in the scan.

The system of embodiments of the invention involves automatically computing the three-dimensional location of the patient by means of a tracking device that may be a tracking marker. The tracking marker may be attached in fixed spatial relation either directly to the fiducial reference, or attached to the fiducial reference via a tracking pole that itself may have a distinct three-dimensional shape. In the dental surgery example, a tracking pole is mechanically connected to the base of the fiducial reference that is in turn fixed in the patient's mouth. Each tracking pole device has a particular observation pattern, located either on itself or on a suitable tracking marker, and a particular geometrical connection to the base, which the computer software recognizes as corresponding to a particular geometry for subsequent location calculations. Although individual tracking pole devices have distinct configurations, they may all share the same connection base and thus may be used with any fiducial reference. The particular tracking information calculations are dictated by the particular tracking pole used, and actual patient location is calculated accordingly. Thus, tracking pole devices may be interchanged and calculation of the location remains the same. This provides, in the case of dental surgery, automatic recognition of the patient head location in space. Alternatively, a sensor device, or a tracker, may be in a known position relative to the fiducial key and its tracking pole, so that the current data image may be mapped to the scan image items.

The fiducial reference and each tracking pole or associated tracking marker may have a pattern made of radio-opaque material so that when imaging information is scanned by the software, the particular items are recognized. Typically, each instrument used in the procedure has a unique pattern on its associated tracking marker so that the tracker information identifies the instrument. The software creates a model of the surgical site, in one embodiment a coordinate system, according to the location and orientation of the patterns on the fiducial reference and/or tracking pole(s) or their attached tracking markers. By way of example, in the embodiment where the fiducial reference has an associated pre-assigned pattern, analysis software interpreting image information from the tracker may recognize the pattern and may select the site of the base of the fiducial to be at the location where the fiducial reference is attached to a splint. If the fiducial key does not have an associated pattern, a fiducial site is designated. In the dental example this may be at a particular spatial relation to the tooth, and a splint location may be automatically designed for placement of the fiducial reference.

In a first aspect of the invention there is provided a surgical monitoring system comprising a fiducial reference configured for removably attaching to a location proximate a surgical site, for having a three-dimensional location and orientation determinable based on scan data of the surgical site, and for having the three-dimensional location and orientation determinable based on image information about the surgical site; a tracker arranged for obtaining the image information; and a controller configured for spatially relating the image information to the scan data and for determining the three-dimensional location and orientation of the fiducial reference. In one embodiment of the invention the fiducial reference may be rigidly and removably attachable to a part of the surgical site. In such an embodiment the fiducial reference may be repeatably attachable in the same three-dimensional orientation to the same location on the particular part of the surgical site.

The fiducial reference is at least one of marked and shaped for having at least one of its location and its orientation determined from the scan data and to allow it to be uniquely identified from the scan data. The surgical monitoring system further comprises a first tracking marker in fixed three-dimensional spatial relationship with the fiducial reference, wherein the first tracking marker is configured for having at least one of its location and its orientation determined by the controller based on the image information and the scan data. The first tracking marker may be configured to be removably and rigidly connected to the fiducial reference by a first tracking pole. The first tracking pole may have a three-dimensional structure uniquely identifiable by the controller from the image information. The three-dimensional structure of the first tracking pole allows its three-dimensional orientation of the first tracking pole to be determined by the controller from the image information.

The first tracking pole and fiducial reference may be configured to allow the first tracking pole to connect to a single unique location on the fiducial reference in a first single unique three-dimensional orientation. The fiducial reference may be configured for the attachment in a single second unique three-dimensional orientation of at least a second tracking pole attached to a second tracking marker. The first tracking marker may have a three-dimensional shape that is uniquely identifiable by the controller from the image information. The first tracking marker may have a three-dimensional shape that allows its three-dimensional orientation to be determined by the controller from the image information. The first tracking marker may have a marking that is uniquely identifiable by the controller and the marking may be configured for allowing at least one of its location and its orientation to be determined by the controller based on the image information and the scan data.

The surgical monitoring system may comprise further tracking markers attached to implements proximate the surgery site and the controller may be configured for determining locations and orientations of the implements based on the image information and information about the further tracking markers.

In another aspect of the invention there is provided a method for relating in real time the three-dimensional location and orientation of a surgical site on a patient to the location and orientation of the surgical site in a scan of the surgical site, the method comprising removably attaching a fiducial reference to a fiducial location on the patient proximate the surgical site; performing the scan with the fiducial reference attached to the fiducial location to obtain scan data; determining the three-dimensional location and orientation of the fiducial reference from the scan data; obtaining real time image information of the surgical site; determining in real time the three-dimensional location and orientation of the fiducial reference from the image information; deriving a spatial transformation matrix for expressing in real time the three-dimensional location and orientation of the fiducial reference as determined from the image information in terms of the three-dimensional location and orientation of the fiducial reference as determined from the scan data.

The obtaining of real time image information of the surgical site may comprise rigidly and removably attaching to the fiducial reference a first tracking marker in a fixed three-dimensional spatial relationship with the fiducial reference. The first tracking marker may be configured for having its location and its orientation determined based on the image information. The attaching of the first tracking marker to the fiducial reference may comprise rigidly and removably attaching the first tracking marker to the fiducial reference by means of a tracking pole. The obtaining of the real time image information of the surgical site may comprise rigidly and removably attaching to the fiducial reference a tracking pole in a fixed three-dimensional spatial relationship with the fiducial reference, and the tracking pole may have a distinctly identifiable three-dimensional shape that allows its location and orientation to be uniquely determined from the image information.

In yet a further aspect of the invention there is provided a method for real time monitoring the position of an object in relation to a surgical site of a patient, the method comprising removably attaching a fiducial reference to a fiducial location on the patient proximate the surgical site; performing a scan with the fiducial reference attached to the fiducial location to obtain scan data; determining the three-dimensional location and orientation of the fiducial reference from the scan data; obtaining real time image information of the surgical site; determining in real time the three-dimensional location and orientation of the fiducial reference from the image information; deriving a spatial transformation matrix for expressing in real time the three-dimensional location and orientation of the fiducial reference as determined from the image information in terms of the three-dimensional location and orientation of the fiducial reference as determined from the scan data; determining in real time the three-dimensional location and orientation of the object from the image information; and relating the three-dimensional location and orientation of the object to the three-dimensional location and orientation of the fiducial reference as determined from the image information. The determining in real time of the three-dimensional location and orientation of the object from the image information may comprise rigidly attaching a tracking marker to the object.

In one alternative embodiment, the tracker itself is attached to the fiducial reference so that the location of an object having a marker may be observed from a known position. The tracker may be a non-stereo tracker and may in particular be a non-stereo optical tracker. In some embodiments the tracker may be a non-stereo tracker employing a plurality of sensor devices.

In a further aspect of the invention, a position monitoring system is provided for a surgical procedure comprising: a single fiducial reference comprising a fiducial key and a fiducial extension rigidly and removably attached to the fiducial key, the fiducial key adapted to be fixed to an area of surgical patient; a first marker attached to the fiducial key in a predetermined fixed relative position and orientation; a non-stereo optical tracker able to determine the position and orientation of the first marker; a computer system having scan data of the patient with the fiducial reference fixed to the area of surgical patient, the computer system coupled to the tracker and including a processor with memory and a software program having a series of instructions which when executed by the processor determines the relative position and orientation of the first marker based on image information from the tracker, and relates the current position and orientation of the fiducial reference to the scan data; and a display system in communication with the computer system, the display system adapted to show the current position and orientation of the fiducial reference relative to the patient scan data during the surgical procedure. The fiducial key may be configured and arranged to fit the part of the patient being scanned. The first marker may be attached to the fiducial key by means of a tracking pole. The fiducial extension may comprise the tracking pole and the tracking pole may be at least one of shaped and marked to be identifiable in the scan data.

The fiducial key may be fixed to the area of the surgical patient such that the fiducial reference is at least partially non-visible during the surgical procedure. At least one of the fiducial key and the fiducial extension may consist of a specific material that is distinctly identifiable in at least one of an X-ray image, Magnetic Resonance Image (MRI), computerized tomograph (CT), sonograph, and cone beam computerized tomograph (CBCT). At least one of the fiducial key and the fiducial extension may have a distinct shape which allows its position and orientation to be determined from the scan data. In other embodiments, at least one of the fiducial key and the fiducial extension may have a label in a predetermined position such that the orientation of the fiducial reference is determined from the scan data. The first marker may one of shaped or marked to be identifiable in the scan and the scan data may comprise data of a scan obtained with the marker attached to the fiducial key.

In a further aspect of the invention, the system may further comprise a multipodal screw fixture for fixing the fiducial key to the area of the surgical patient. The multipodal screw fixture may be monolithically integrated with the fiducial key.

In a further aspect of the invention, a method is provided for monitoring a surgical site, comprising: attaching a fiducial key to a location proximate to a surgical site; rigidly and removably attaching a fiducial extension to the fiducial key; creating a first scan of the surgical location with the fiducial key attached to the location proximate to a surgical site and the fiducial extension rigidly and removably attached to the fiducial key; rigidly attaching a marker to the fiducial key; obtaining image information from a non-stereo optical tracker proximate the surgical site; communicating the image information from the optical tracker to a computing device; and calculating and displaying a model of the surgical site by means of the computing device based on the scan, the identity of at least one of the fiducial key and the fiducial extension, and the image information received from said tracker. The attaching the fiducial key may comprise multipodally attaching the fiducial key by means of a surgical screw and a plurality of surgical nails.

BRIEF DESCRIPTION OF THE DRAWINGS

The above mentioned and other features and objects of this invention, and the manner of attaining them, will become more apparent and the invention itself will be better understood by reference to the following description of an embodiment of the invention taken in conjunction with the accompanying drawings, wherein.

Figure 1:
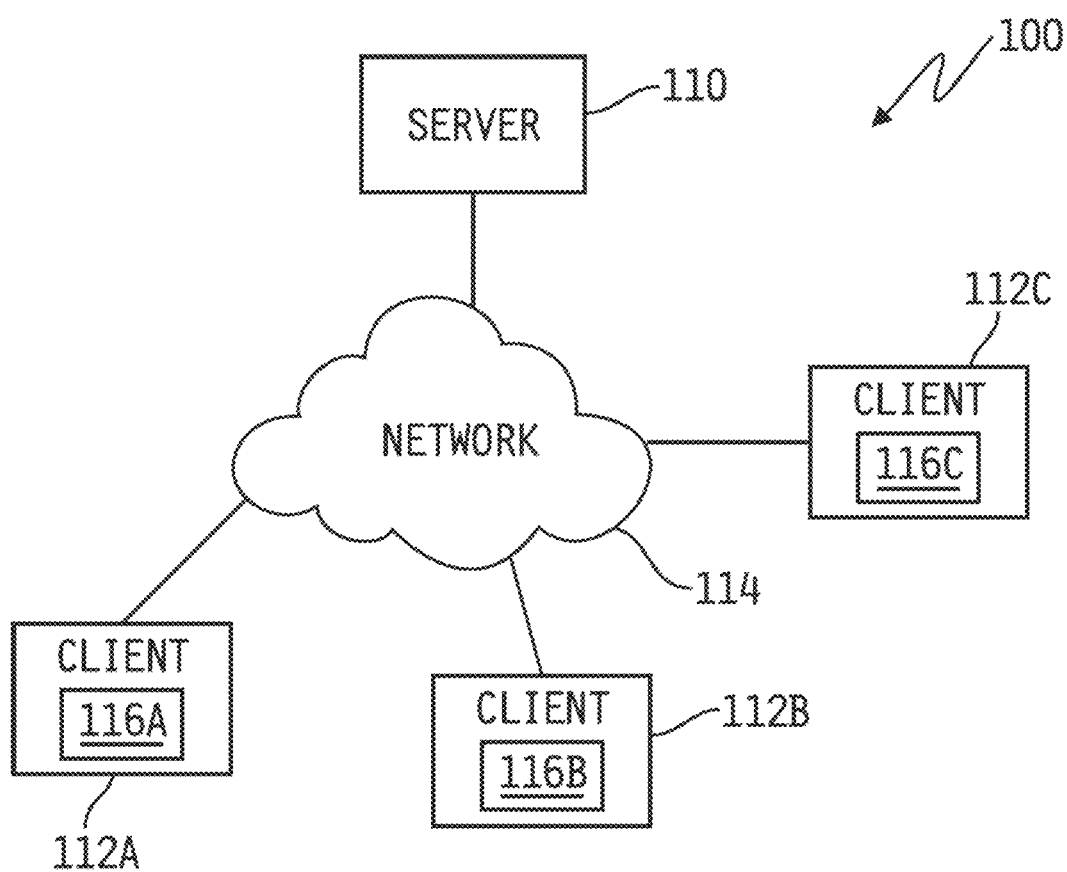
FIG. 1 is a schematic diagrammatic view of a network system in which embodiments of the present invention may be utilized.

Corresponding reference characters indicate corresponding parts throughout the several views. Although the drawings represent embodiments of the present invention, the drawings are not necessarily to scale and certain features may be exaggerated in order to better illustrate and explain the present invention. The flow charts and screen shots are also representative in nature, and actual embodiments of the invention may include further features or steps not shown in the drawings. The exemplification set out herein illustrates an embodiment of the invention, in one form, and such exemplifications are not to be construed as limiting the scope of the invention in any manner.

DESCRIPTION OF EMBODIMENTS OF THE PRESENT INVENTION

The embodiments disclosed below are not intended to be exhaustive or limit the invention to the precise form disclosed in the following detailed description. Rather, the embodiments are chosen and described so that others skilled in the art may utilize their teachings.

The detailed descriptions that follow are presented in part in terms of algorithms and symbolic representations of operations on data bits within a computer memory representing alphanumeric characters or other information. The hardware components are shown with particular shapes and relative orientations and sizes using particular scanning techniques, although in the general case one of ordinary skill recognizes that a variety of particular shapes and orientations and scanning methodologies may be used within the teaching of the present invention. A computer generally includes a processor for executing instructions and memory for storing instructions and data, including interfaces to obtain and process imaging data. When a general-purpose computer has a series of machine encoded instructions stored in its memory, the computer operating on such encoded instructions may become a specific type of machine, namely a computer particularly configured to perform the operations embodied by the series of instructions. Some of the instructions may be adapted to produce signals that control operation of other machines and thus may operate through those control signals to transform materials far removed from the computer itself. These descriptions and representations are the means used by those skilled in the art of data processing arts to most effectively convey the substance of their work to others skilled in the art.

An algorithm is here, and generally, conceived to be a self-consistent sequence of steps leading to a desired result. These steps are those requiring physical manipulations of physical quantities, observing and measuring scanned data representative of matter around the surgical site. Usually, though not necessarily, these quantities take the form of electrical or magnetic pulses or signals capable of being stored, transferred, transformed, combined, compared, and otherwise manipulated. It proves convenient at times, principally for reasons of common usage, to refer to these signals as bits, values, symbols, characters, display data, terms, numbers, or the like as a reference to the physical items or manifestations in which such signals are embodied or expressed to capture the underlying data of an image. It should be borne in mind, however, that all of these and similar terms are to be associated with the appropriate physical quantities and are merely used here as convenient labels applied to these quantities.

Some algorithms may use data structures for both inputting information and producing the desired result. Data structures greatly facilitate data management by data processing systems, and are not accessible except through sophisticated software systems. Data structures are not the information content of a memory, rather they represent specific electronic structural elements that impart or manifest a physical organization on the information stored in memory. More than mere abstraction, the data structures are specific electrical or magnetic structural elements in memory, which simultaneously represent complex data accurately, often data modeling physical characteristics of related items, and provide increased efficiency in computer operation.

Further, the manipulations performed are often referred to in terms, such as comparing or adding, commonly associated with mental operations performed by a human operator. No such capability of a human operator is necessary, or desirable in most cases, in any of the operations described herein that form part of the present invention; the operations are machine operations. Useful machines for performing the operations of the present invention include general-purpose digital computers or other similar devices. In all cases the distinction between the method operations in operating a computer and the method of computation itself should be recognized. The present invention relates to a method and apparatus for operating a computer in processing electrical or other (e.g., mechanical, chemical) physical signals to generate other desired physical manifestations or signals. The computer operates on software modules, which are collections of signals stored on a media that represents a series of machine instructions that enable the computer processor to perform the machine instructions that implement the algorithmic steps. Such machine instructions may be the actual computer code the processor interprets to implement the instructions, or alternatively may be a higher level coding of the instructions that is interpreted to obtain the actual computer code. The software module may also include a hardware component, wherein some aspects of the algorithm are performed by the circuitry itself rather as a result of an instruction.

The present invention also relates to an apparatus for performing these operations. This apparatus may be specifically constructed for the required purposes or it may comprise a general-purpose computer as selectively activated or reconfigured by a computer program stored in the computer. The algorithms presented herein are not inherently related to any particular computer or other apparatus unless explicitly indicated as requiring particular hardware. In some cases, the computer programs may communicate or relate to other programs or equipments through signals configured to particular protocols, which may or may not require specific hardware or programming to interact. In particular, various general-purpose machines may be used with programs written in accordance with the teachings herein, or it may prove more convenient to construct more specialized apparatus to perform the required method steps. The required structure for a variety of these machines will appear from the description below.

The present invention may deal with "object-oriented" software, and particularly with an "object-oriented" operating system. The "object-oriented" software is organized into "objects", each comprising a block of computer instructions describing various procedures ("methods") to be performed in response to "messages" sent to the object or "events" which occur with the object. Such operations include, for example, the manipulation of variables, the activation of an object by an external event, and the transmission of one or more messages to other objects. Often, but not necessarily, a physical object has a corresponding software object that may collect and transmit observed data from the physical device to the software system. Such observed data may be accessed from the physical object and/or the software object merely as an item of convenience; therefore where "actual data" is used in the following description, such "actual data" may be from the instrument itself or from the corresponding software object or module.

Messages are sent and received between objects having certain functions and knowledge to carry out processes. Messages are generated in response to user instructions, for example, by a user activating an icon with a "mouse" pointer generating an event. Also, messages may be generated by an object in response to the receipt of a message. When one of the objects receives a message, the object carries out an operation (a message procedure) corresponding to the message and, if necessary, returns a result of the operation. Each object has a region where internal states (instance variables) of the object itself are stored and where the other objects are not allowed to access. One feature of the object-oriented system is inheritance. For example, an object for drawing a "circle" on a display may inherit functions and knowledge from another object for drawing a "shape" on a display.

A programmer "programs" in an object-oriented programming language by writing individual blocks of code each of which creates an object by defining its methods. A collection of such objects adapted to communicate with one another by means of messages comprises an object-oriented program. Object-oriented computer programming facilitates the modeling of interactive systems in that each component of the system may be modeled with an object, the behavior of each component being simulated by the methods of its corresponding object, and the interactions between components being simulated by messages transmitted between objects.

An operator may stimulate a collection of interrelated objects comprising an object-oriented program by sending a message to one of the objects. The receipt of the message may cause the object to respond by carrying out predetermined functions, which may include sending additional messages to one or more other objects. The other objects may in turn carry out additional functions in response to the messages they receive, including sending still more messages. In this manner, sequences of message and response may continue indefinitely or may come to an end when all messages have been responded to and no new messages are being sent. When modeling systems utilizing an object-oriented language, a programmer need only think in terms of how each component of a modeled system responds to a stimulus and not in terms of the sequence of operations to be performed in response to some stimulus. Such sequence of operations naturally flows out of the interactions between the objects in response to the stimulus and need not be preordained by the programmer.

Although object-oriented programming makes simulation of systems of interrelated components more intuitive, the operation of an object-oriented program is often difficult to understand because the sequence of operations carried out by an object-oriented program is usually not immediately apparent from a software listing as in the case for sequentially organized programs. Nor is it easy to determine how an object-oriented program works through observation of the readily apparent manifestations of its operation. Most of the operations carried out by a computer in response to a program are "invisible" to an observer since only a relatively few steps in a program typically produce an observable computer output.

In the following description, several terms that are used frequently have specialized meanings in the present context. The term "object" relates to a set of computer instructions and associated data, which may be activated directly or indirectly by the user. The terms "windowing environment", "running in windows", and "object oriented operating system" are used to denote a computer user interface in which information is manipulated and displayed on a video display such as within bounded regions on a raster scanned video display. The terms "network", "local area network", "LAN", "wide area network", or "WAN" mean two or more computers that are connected in such a manner that messages may be transmitted between the computers. In such computer networks, typically one or more computers operate as a "server", a computer with large storage devices such as hard disk drives and communication hardware to operate peripheral devices such as printers or modems. Other computers, termed "workstations", provide a user interface so that users of computer networks may access the network resources, such as shared data files, common peripheral devices, and inter-workstation communication. Users activate computer programs or network resources to create "processes" which include both the general operation of the computer program along with specific operating characteristics determined by input variables and its environment. Similar to a process is an agent (sometimes called an intelligent agent), which is a process that gathers information or performs some other service without user intervention and on some regular schedule. Typically, an agent, using parameters typically provided by the user, searches locations either on the host machine or at some other point on a network, gathers the information relevant to the purpose of the agent, and presents it to the user on a periodic basis.

The term "desktop" means a specific user interface which presents a menu or display of objects with associated settings for the user associated with the desktop. When the desktop accesses a network resource, which typically requires an application program to execute on the remote server, the desktop calls an Application Program Interface, or "API", to allow the user to provide commands to the network resource and observe any output. The term "Browser" refers to a program which is not necessarily apparent to the user, but which is responsible for transmitting messages between the desktop and the network server and for displaying and interacting with the network user. Browsers are designed to utilize a communications protocol for transmission of text and graphic information over a worldwide network of computers, namely the "World Wide Web" or simply the "Web". Examples of Browsers compatible with the present invention include the Internet Explorer program sold by Microsoft Corporation (Internet Explorer is a trademark of Microsoft Corporation), the Opera Browser program created by Opera Software ASA, or the Firefox browser program distributed by the Mozilla Foundation (Firefox is a registered trademark of the Mozilla Foundation). Although the following description details such operations in terms of a graphic user interface of a Browser, the present invention may be practiced with text based interfaces, or even with voice or visually activated interfaces, that have many of the functions of a graphic based Browser.

Browsers display information, which is formatted in a Standard Generalized Markup Language ("SGML") or a HyperText Markup Language ("HTML"), both being scripting languages, which embed non-visual codes in a text document through the use of special ASCII text codes. Files in these formats may be easily transmitted across computer networks, including global information networks like the Internet, and allow the Browsers to display text, images, and play audio and video recordings. The Web utilizes these data file formats to conjunction with its communication protocol to transmit such information between servers and workstations. Browsers may also be programmed to display information provided in an eXtensible Markup Language ("XML") file, with XML files being capable of use with several Document Type Definitions ("DTD") and thus more general in nature than SGML or HTML. The XML file may be analogized to an object, as the data and the stylesheet formatting are separately contained (formatting may be thought of as methods of displaying information, thus an XML file has data and an associated method).

The terms "personal digital assistant" or "PDA", as defined above, means any handheld, mobile device that combines computing, telephone, fax, e-mail and networking features. The terms "wireless wide area network" or "WWAN" mean a wireless network that serves as the medium for the transmission of data between a handheld device and a computer. The term "synchronization" means the exchanging of information between a first device, e.g. a handheld device, and a second device, e.g. a desktop computer, either via wires or wirelessly. Synchronization ensures that the data on both devices are identical (at least at the time of synchronization).

In wireless wide area networks, communication primarily occurs through the transmission of radio signals over analog, digital cellular, or personal communications service ("PCS") networks. Signals may also be transmitted through microwaves and other electromagnetic waves. At the present time, most wireless data communication takes place across cellular systems using second generation technology such as code-division multiple access ("CDMA"), time division multiple access ("TDMA"), the Global System for Mobile Communications ("GSM"), Third Generation (wideband or "3G"), Fourth Generation (broadband or "4G"), personal digital cellular ("PDC"), or through packet-data technology over analog systems such as cellular digital packet data (CDPD") used on the Advance Mobile Phone Service ("AMPS").

The terms "wireless application protocol" or "WAP" mean a universal specification to facilitate the delivery and presentation of web-based data on handheld and mobile devices with small user interfaces. "Mobile Software" refers to the software operating system, which allows for application programs to be implemented on a mobile device such as a mobile telephone or PDA. Examples of Mobile Software are Java and Java ME (Java and JavaME are trademarks of Sun Microsystems, Inc. of Santa Clara, Calif.), BREW (BREW is a registered trademark of Qualcomm Incorporated of San Diego, Calif.), Windows Mobile (Windows is a registered trademark of Microsoft Corporation of Redmond, Wash.), Palm OS (Palm is a registered trademark of Palm, Inc. of Sunnyvale, Calif.), Symbian OS (Symbian is a registered trademark of Symbian Software Limited Corporation of London, United Kingdom), ANDROID OS (ANDROID is a registered trademark of Google, Inc. of Mountain View, Calif.), and iPhone OS (iPhone is a registered trademark of Apple, Inc. of Cupertino, Calif.), and Windows Phone 7. "Mobile Apps" refers to software programs written for execution with Mobile Software.

The terms "scan," "fiducial reference", "fiducial location", "marker," "tracker" and "image information" have particular meanings in the present disclosure. For purposes of the present disclosure, "scan" or derivatives thereof refer to x-ray, magnetic resonance imaging (MRI), computerized tomography (CT), sonography, cone beam computerized tomography (CBCT), or any system that produces a quantitative spatial representation of a patient. The term "fiducial reference" or simply "fiducial" refers to an object or reference on the image of a scan that is uniquely identifiable as a fixed recognizable point. In the present specification the term "fiducial location" refers to a useful location to which a fiducial reference is attached. A "fiducial location" will typically be proximate a surgical site. The term "marker" or "tracking marker" refers to an object or reference that may be perceived by a sensor proximate to the location of the surgical or dental procedure, where the sensor may be an optical sensor, a radio frequency identifier (RFID), a sonic motion detector, an ultra-violet or infrared sensor. The term "tracker" refers to a device or system of devices able to determine the location of the markers and their orientation and movement continually in 'real time' during a procedure. As an example of a possible implementation, if the markers are composed of printed targets then the tracker may include a stereo camera pair. The tracker may include a non-stereo optical camera or a stereo camera pair, which may operate in the visible or infrared region of the spectrum. The term "image information" is used in the present specification to describe information obtained by the tracker, whether optical or otherwise, about one or more tracking markers and usable for determining the location of the markers and their orientation and movement continually in 'real time' during a procedure.

FIG. 1 is a high-level block diagram of a computing environment 100 according to one embodiment. FIG. 1 illustrates server 110 and three clients 112 connected by network 114. Only three clients 112 are shown in FIG. 1 in order to simplify and clarify the description. Embodiments of the computing environment 100 may have thousands or millions of clients 112 connected to network 114, for example the Internet. Users (not shown) may operate software 116 on one of clients 112 to both send and receive messages network 114 via server 110 and its associated communications equipment and software (not shown).

Figure 2:
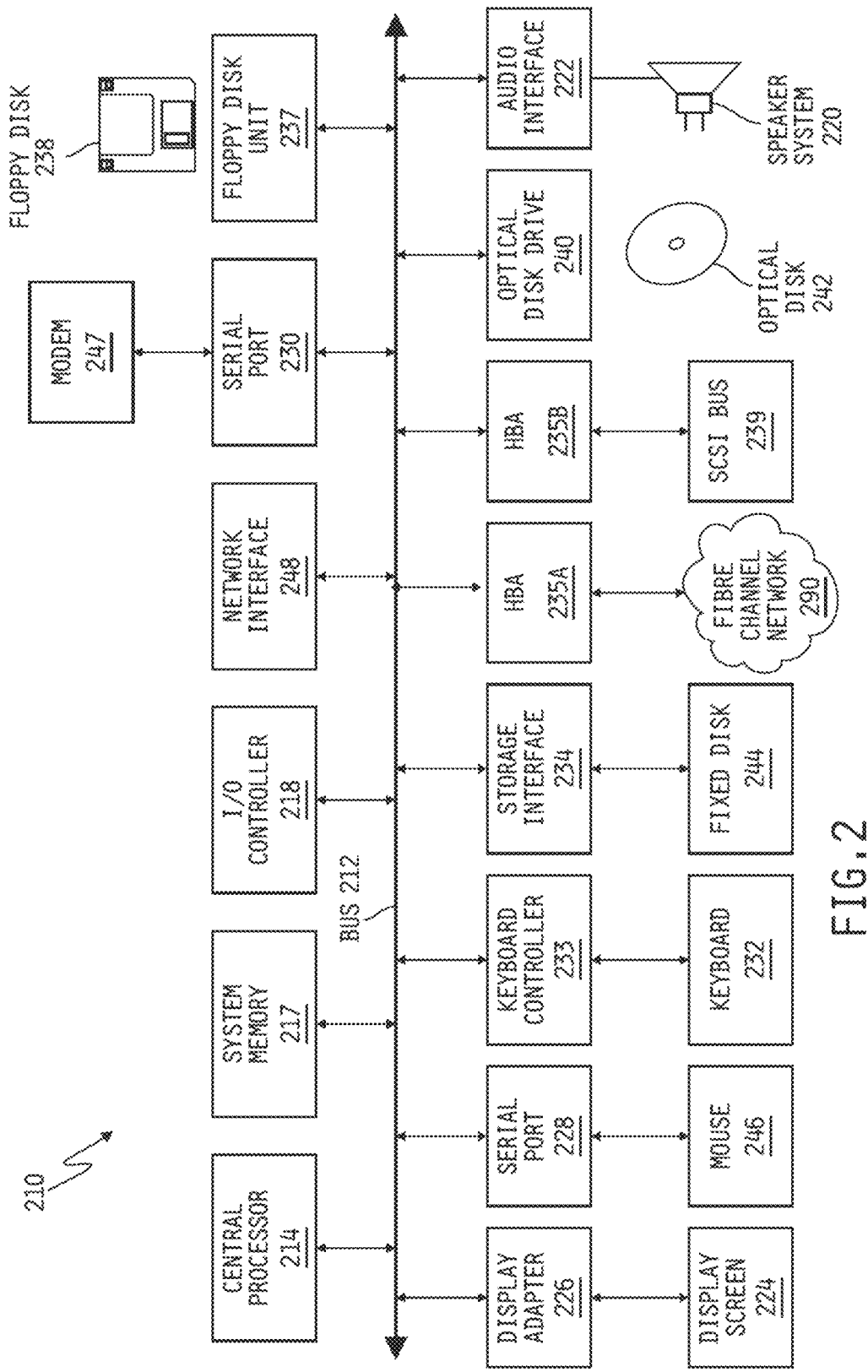
FIG. 2 is a block diagram of a computing system (either a server or client, or both, as appropriate), with optional input devices (e.g., keyboard, mouse, touch screen, etc.) and output devices, hardware, network connections, one or more processors, and memory/storage for data and modules, etc. which may be utilized as controller and display in conjunction with embodiments of the present invention.

FIG. 2 depicts a block diagram of computer system 210 suitable for implementing server 110 or client 112. Computer system 210 includes bus 212 which interconnects major subsystems of computer system 210, such as central processor 214, system memory 217 (typically RAM, but which may also include ROM, flash RAM, or the like), input/output controller 218, external audio device, such as speaker system 220 via audio output interface 222, external device, such as display screen 224 via display adapter 226, serial ports 228 and 230, keyboard 232 (interfaced with keyboard controller 233), storage interface 234, disk drive 237 operative to receive floppy disk 238 or other nonvolatile computer memory device (e.g., flash memory such as memory sticks, cards, USB drives, solid-state drives, etc.), host bus adapter (HBA) interface card 235A operative to connect with Fibre Channel network 290, host bus adapter (HBA) interface card 235B operative to connect to SCSI bus 239, and optical disk drive 240 operative to receive optical disk 242. Also included are mouse 246 (or other point-and-click device, coupled to bus 212 via serial port 228), modem 247 (coupled to bus 212 via serial port 230), and network interface 248 (coupled directly to bus 212).

Bus 212 allows data communication between central processor 214 and system memory 217, which may include read-only memory (ROM) or flash memory (neither shown), and random access memory (RAM) (not shown), as previously noted. RAM is generally the main memory into which operating system and application programs are loaded. ROM or flash memory may contain, among other software code, Basic Input-Output system (BIOS), which controls basic hardware operation such as interaction with peripheral components. Applications resident with computer system 210 are generally stored on and accessed via computer readable media, such as hard disk drives (e.g., fixed disk 244), optical drives (e.g., optical drive 240), floppy disk unit 237, or other storage medium. Additionally, applications may be in the form of electronic signals modulated in accordance with the application and data communication technology when accessed via network modem 247 or interface 248 or other telecommunications equipment (not shown).

Storage interface 234, as with other storage interfaces of computer system 210, may connect to standard computer readable media for storage and/or retrieval of information, such as fixed disk drive 244. Fixed disk drive 244 may be part of computer system 210 or may be separate and accessed through other interface systems. Modem 247 may provide direct connection to remote servers via telephone link or the Internet via an Internet service provider (ISP) (not shown). Network interface 248 may provide direct connection to remote servers via direct network link to the Internet via a POP (point of presence). Network interface 248 may provide such connection using wireless techniques, including digital cellular telephone connection, Cellular Digital Packet Data (CDPD) connection, digital satellite data connection or the like.

Figure 3A:
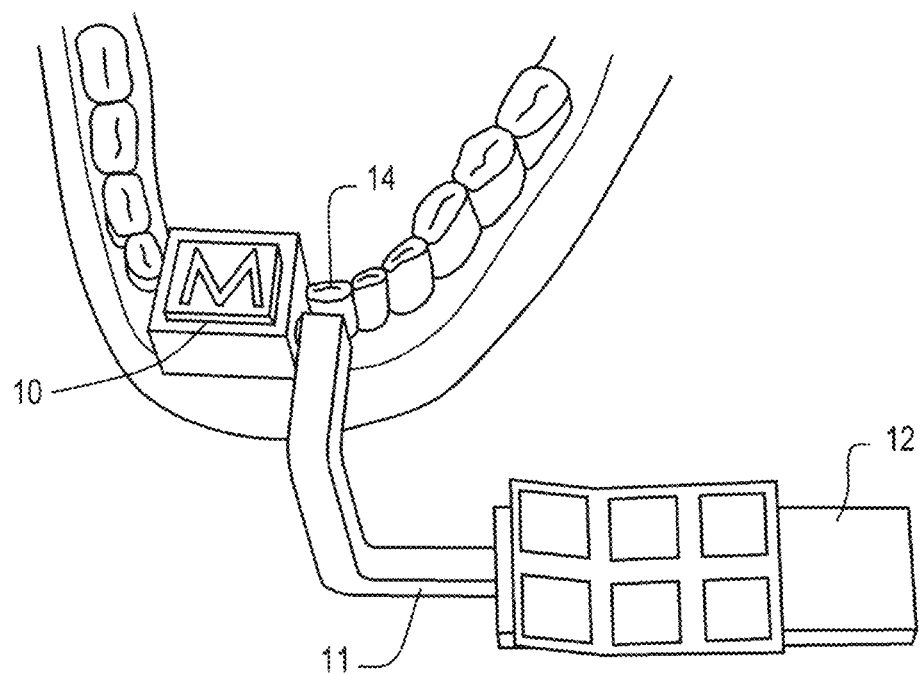
FIGS. 3A-N are drawings of hardware components of the surgical monitoring system according to embodiments of the invention.
Figure 3B:
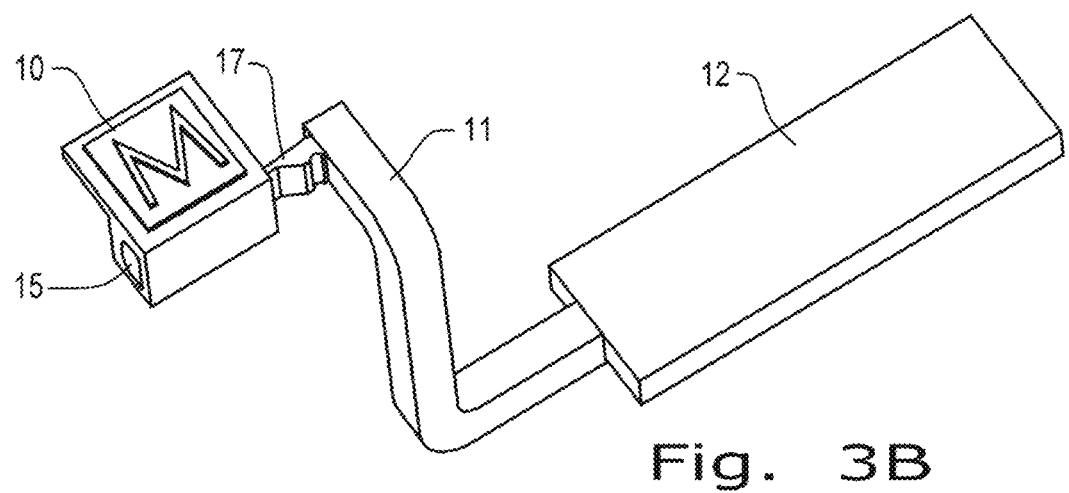
Figure 3C:
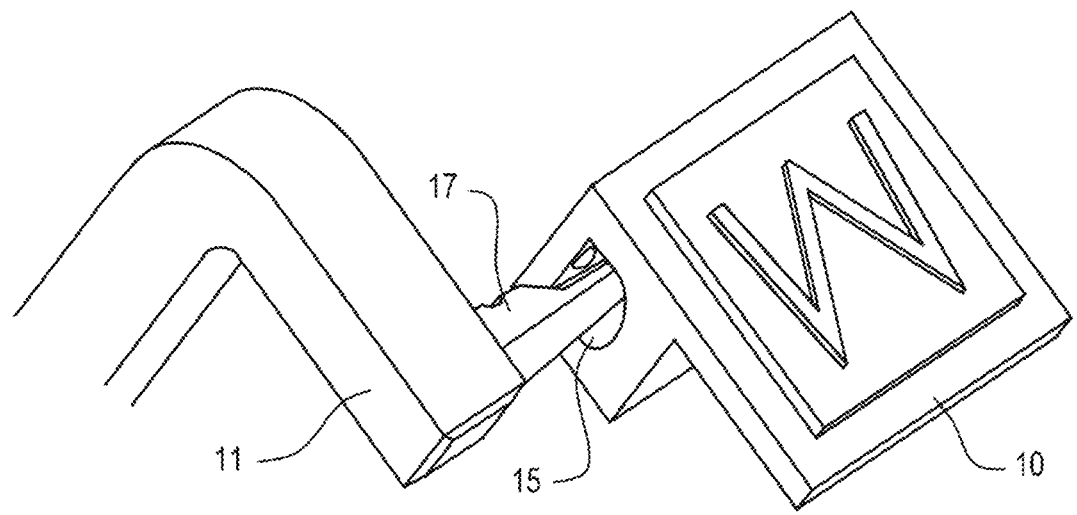
Figure 3D:
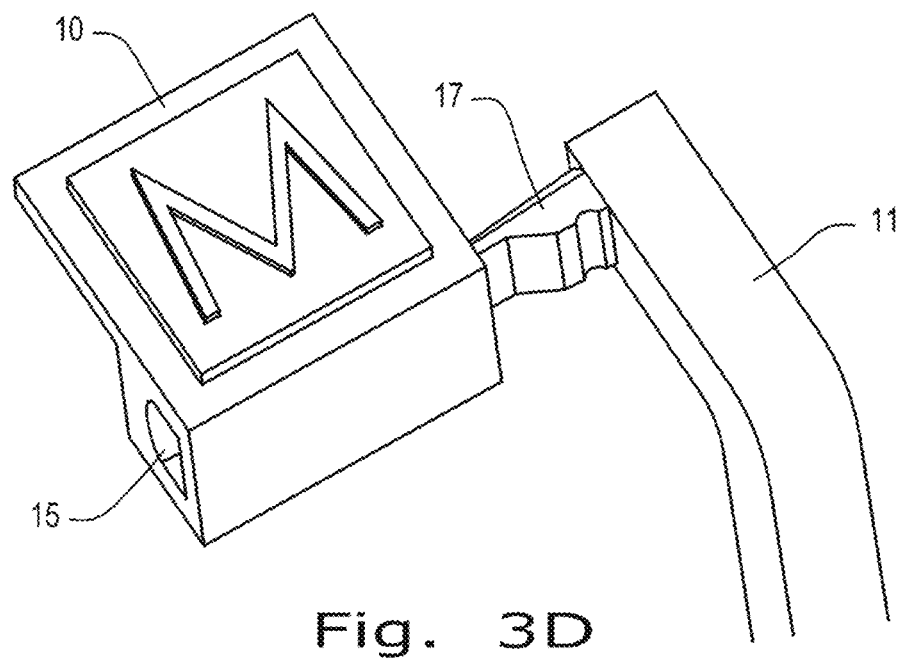
Figure 3E:
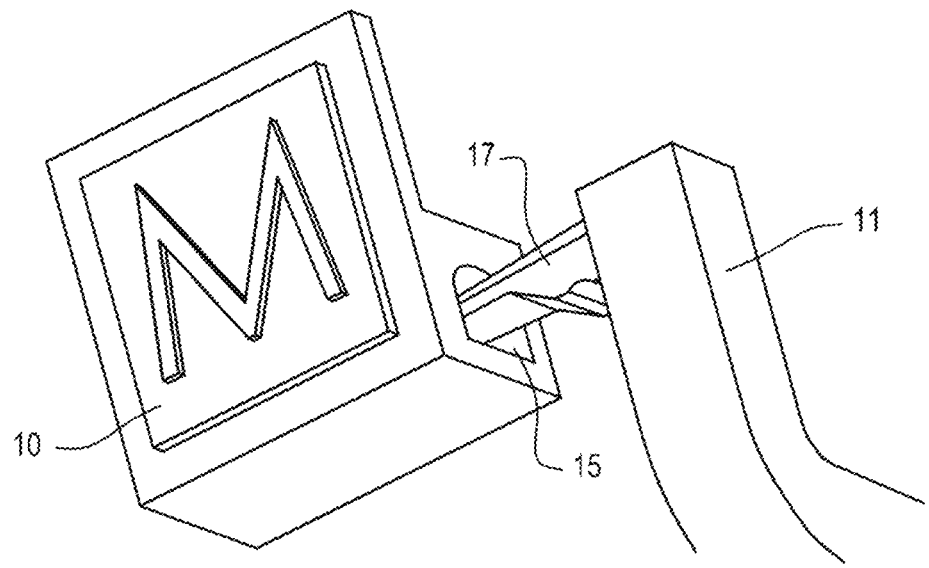
Figure 3F:
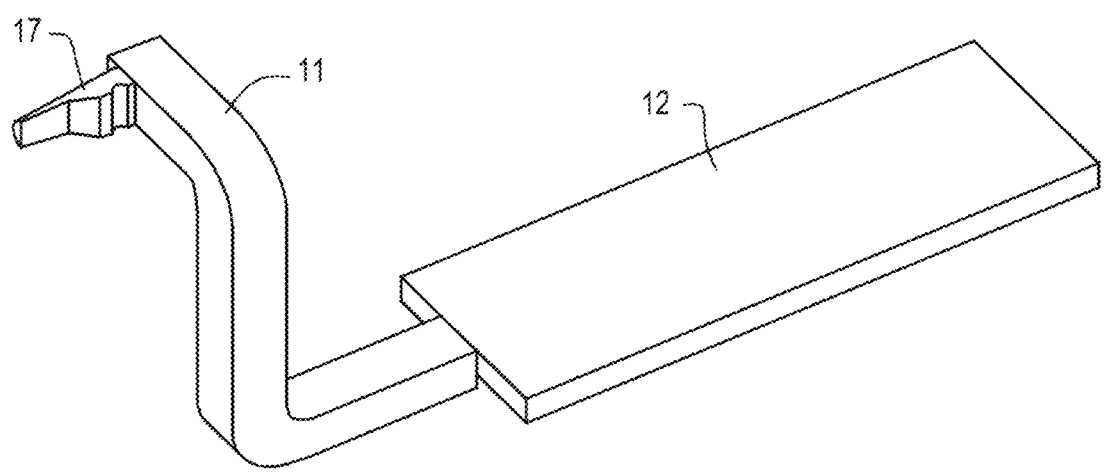
Figure 3G:
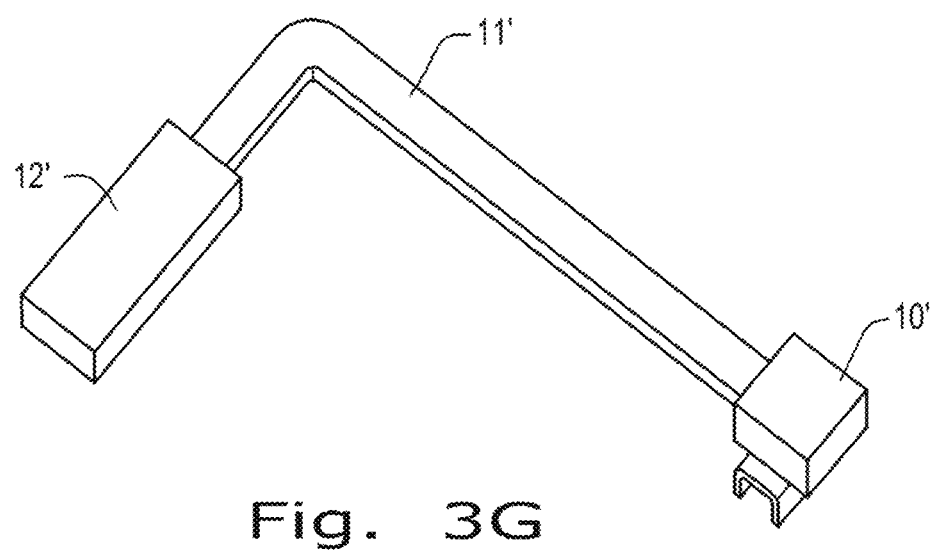
Figure 3H:
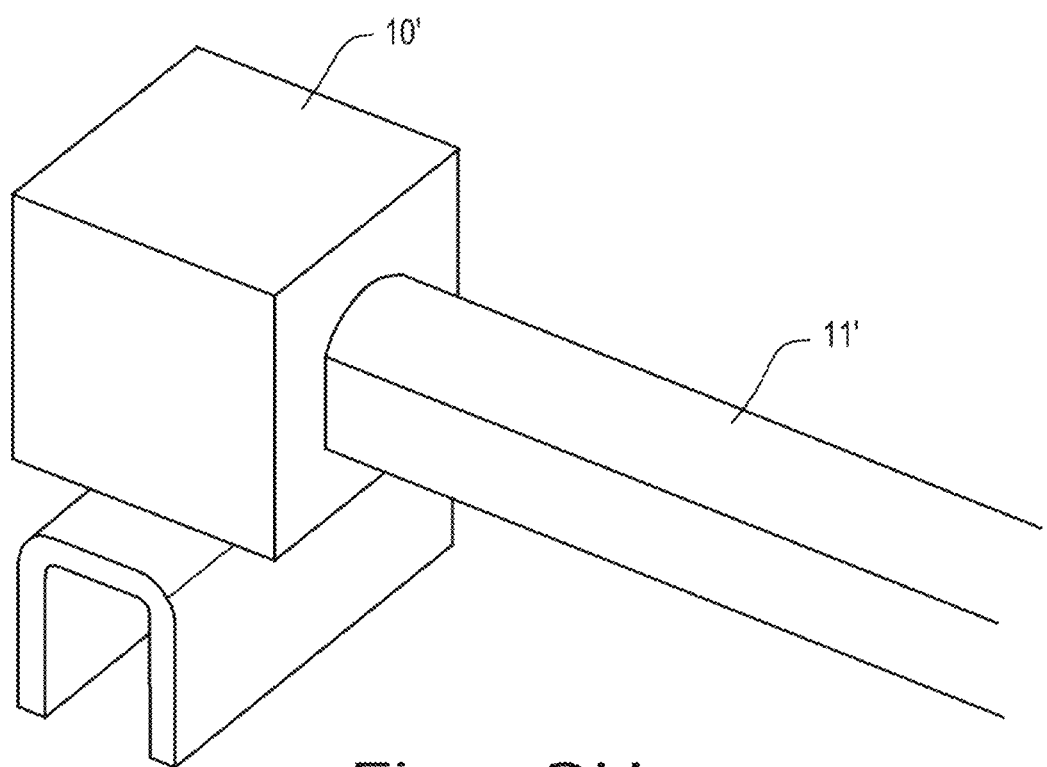
Figure 3I:
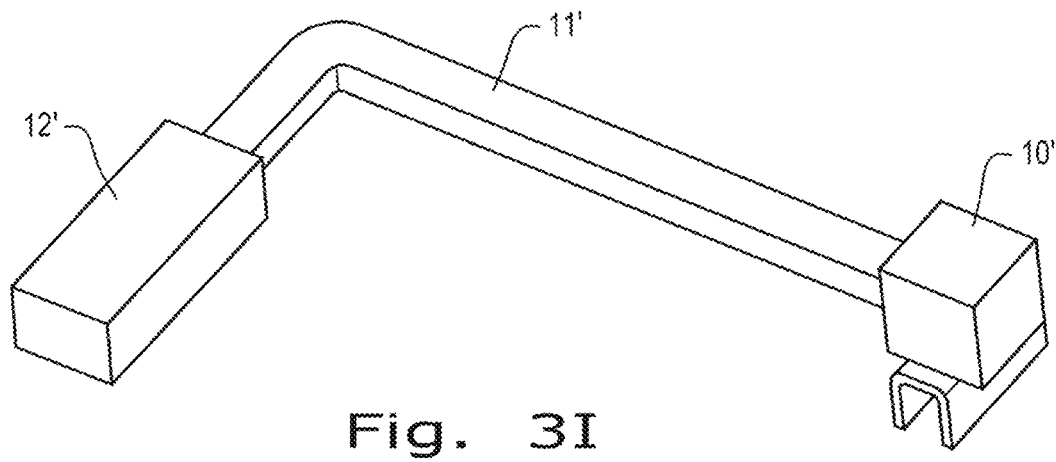
Figure 3J:
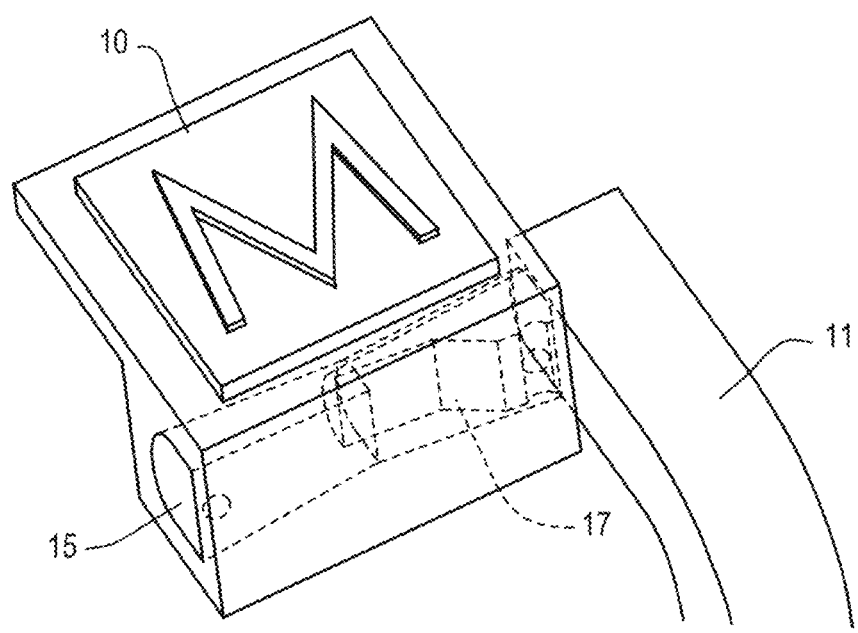
Figure 3K:
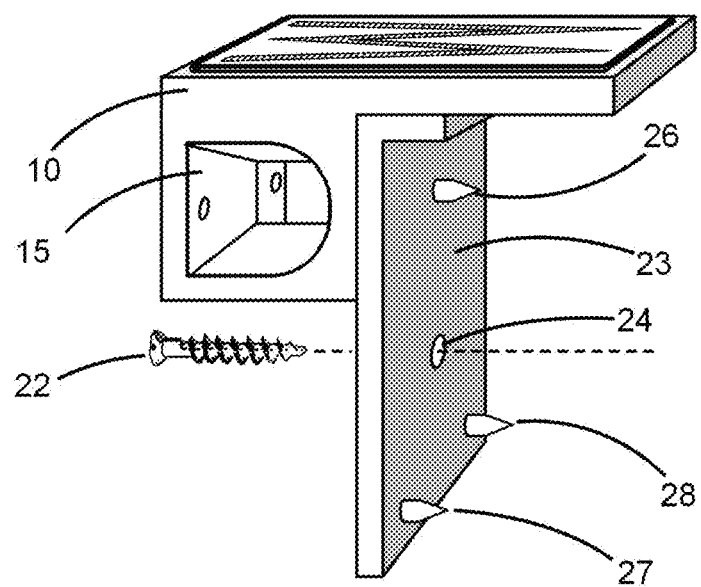
Figure 3L:
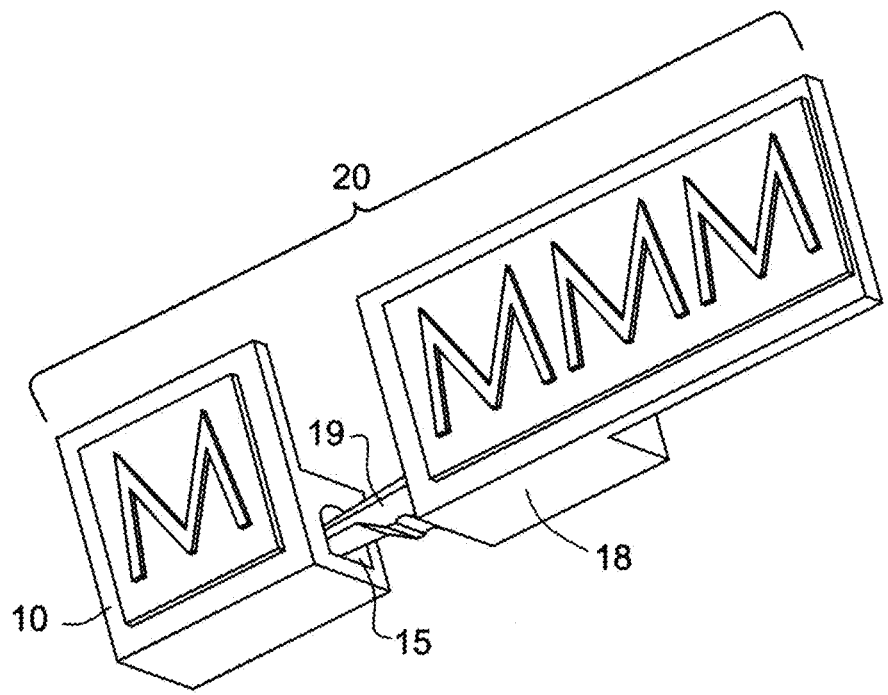
Figure 3M:
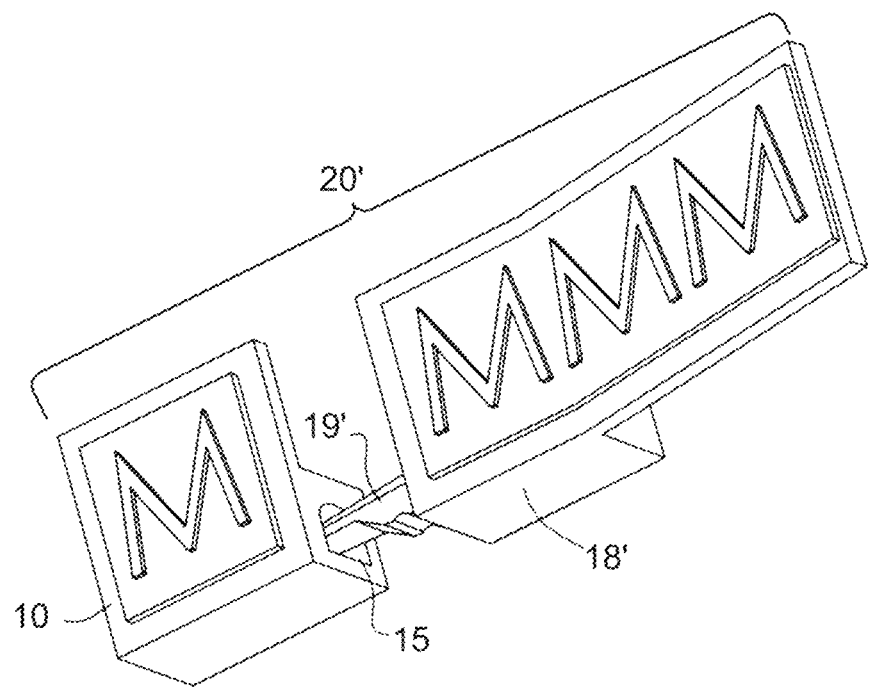
Figure 3N:
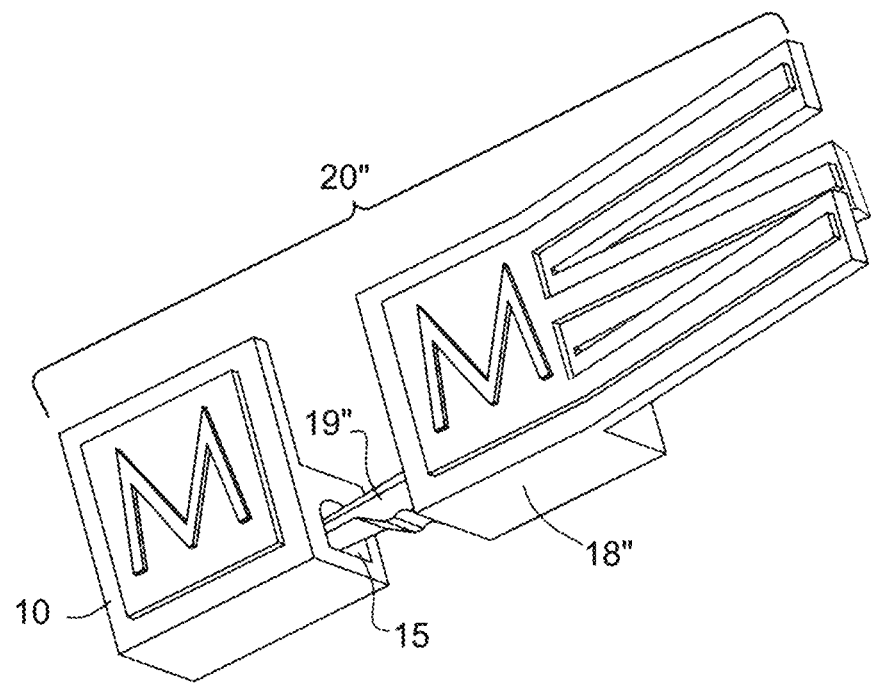

Many other devices or subsystems (not shown) may be connected in a similar manner (e.g., document scanners, digital cameras and so on), including the hardware components of FIGS. 3A-N, which alternatively may be in communication with associated computational resources through local, wide-area, or wireless networks or communications systems. Thus, while the disclosure may generally discuss an embodiment where the hardware components are directly connected to computing resources, one of ordinary skill in this area recognizes that such hardware may be remotely connected with computing resources. Conversely, all of the devices shown in FIG. 2 need not be present to practice the present disclosure. Devices and subsystems may be interconnected in different ways from that shown in FIG. 2. Operation of a computer system such as that shown in FIG. 2 is readily known in the art and is not discussed in detail in this application. Software source and/or object codes to implement the present disclosure may be stored in computer-readable storage media such as one or more of system memory 217, fixed disk 244, optical disk 242, or floppy disk 238. The operating system provided on computer system 210 may be a variety or version of either MS-DOS® (MS-DOS is a registered trademark of Microsoft Corporation of Redmond, Wash.), WINDOWS® (WINDOWS is a registered trademark of Microsoft Corporation of Redmond, Wash.), OS/2® (OS/2 is a registered trademark of International Business Machines Corporation of Armonk, N.Y.), UNIX® (UNIX is a registered trademark of X/Open Company Limited of Reading, United Kingdom), Linux® (Linux is a registered trademark of Linus Torvalds of Portland, Oreg.), or other known or developed operating system.

Moreover, regarding the signals described herein, those skilled in the art recognize that a signal may be directly transmitted from a first block to a second block, or a signal may be modified (e.g., amplified, attenuated, delayed, latched, buffered, inverted, filtered, or otherwise modified) between blocks. Although the signals of the above-described embodiments are characterized as transmitted from one block to the next, other embodiments of the present disclosure may include modified signals in place of such directly transmitted signals as long as the informational and/or functional aspect of the signal is transmitted between blocks. To some extent, a signal input at a second block may be conceptualized as a second signal derived from a first signal output from a first block due to physical limitations of the circuitry involved (e.g., there will inevitably be some attenuation and delay). Therefore, as used herein, a second signal derived from a first signal includes the first signal or any modifications to the first signal, whether due to circuit limitations or due to passage through other circuit elements which do not change the informational and/or final functional aspect of the first signal.

The present invention relates to a surgical hardware and software monitoring system and method which allows for surgical planning while the patient is available for surgery, for example while the patient is being prepared for surgery so that the system may model the surgical site. The system uses a particularly configured piece of hardware, namely a fiducial reference, represented as fiducial key 10 in FIG. 3A, to orient tracking marker 12 of the monitoring system with regard to the critical area of the surgery. Fiducial key 10 is attached to a location near the intended surgical area, in the exemplary embodiment of the dental surgical area of FIG. 3A, fiducial key 10 is attached to a dental splint 14. Tracking marker 12 may be connected to fiducial key 10 by tracking pole 11. In embodiments in which the fiducial reference is directly visible to a suitable tracker (see for example FIG. 5 and FIG. 6) that acquires image information about the surgical site, a tracking marker may be attached directly to the fiducial reference, being fiducial key 10 in the present embodiment. For example a dental surgery, the dental tracking marker 14 may be used to securely locate the fiducial 10 near the surgical area. The fiducial key 10 may be used as a point of reference, or a fiducial, for the further image processing of data acquired from tracking marker 12 by the tracker. In some applications, the fiducial key 10 may be disposed in a location or in such orientation as to be at least in part non-visible to the tracker of the system.

In other embodiments additional tracking markers 12 may be attached to items independent of the fiducial key 10 and any of its associated tracking poles 11 or tracking markers 12. This allows the independent items to be tracked by the tracker.

In a further embodiment at least one of the items or instruments near the surgical site may optionally have a tracker attached to function as tracker for the monitoring system of the invention and to thereby sense the orientation and the position of the tracking marker 12 and of any other additional tracking markers relative to the scan data of the surgical area. By way of example, the tracker attached to an instrument may be a miniature digital camera and it may be attached, for example, to a dentist's drill. Any other markers to be tracked by the tracker attached to the item or instrument must be within the field of view of the tracker.

Using the dental surgery example, the patient is scanned to obtain an initial scan of the surgical site. The particular configuration of fiducial key 10 allows computer software stored in memory and executed in a suitable controller, for example processor 214 and memory 217 of computer 210 of FIG. 2, to recognize its relative position within the surgical site from the scan data, so that further observations may be made with reference to both the location and orientation of fiducial key 10. In some embodiments, the fiducial reference includes a marking that is apparent as a recognizable identifying symbol when scanned. In other embodiments, the fiducial reference includes a shape that is distinct in the sense that the body apparent on the scan has an asymmetrical form allowing the front, rear, upper, and lower, and left/right defined surfaces that may be unambiguously determined from the analysis of the scan, thereby to allow the determination not only of the location of the fiducial reference, but also of its orientation. The marking and/or shape of fiducial key 10 allows it to be used as the single and only fiducial key employed in the surgical hardware and software monitoring system. By comparison, prior art systems typically rely on a plurality of fiducials. Hence, while the tracker may track several tracking markers within the monitoring system, only a single fiducial reference or key 10 of known shape or marking is required. By way of example, FIG. 5, later discussed in more detail, shows markers 506 and 502 tracked by tracker 508, but there is only one fiducial reference or key 502 in the system. FIG. 6 similarly shows three markers 604, 606, and 608 being tracked by tracker 610, while there is only a single fiducial reference or key 602 in the system.

In addition, the computer software may create a coordinate system for organizing objects in the scan, such as teeth, jaw bone, skin and gum tissue, other surgical instruments, etc. The coordinate system relates the images on the scan to the space around the fiducial and locates the instruments bearing tracking markers both by orientation and position. The model generated by the monitoring system may then be used to check boundary conditions, and in conjunction with the tracker display the arrangement in real time on a suitable display, for example display 224 of FIG. 2.

In one embodiment, the computer system has a predetermined knowledge of the physical configuration of fiducial key 10 and examines slices/sections of the scan to locate fiducial key 10. Locating of fiducial key 10 may be on the basis of its distinct shape, or on the basis of distinctive identifying and orienting markings upon the fiducial key or on attachments to the fiducial key 10 as tracking marker 12. Fiducial key 10 may be rendered distinctly visible in the scans through higher imaging contrast by the employ of radio-opaque materials or high-density materials in the construction of the fiducial key 10. In other embodiments the material of the distinctive identifying and orienting markings may be created using suitable high density or radio-opaque inks or materials.

Once fiducial key 10 is identified, the location and orientation of the fiducial key 10 is determined from the scan segments, and a point within fiducial key 10 is assigned as the center of the coordinate system. The point so chosen may be chosen arbitrarily, or the choice may be based on some useful criterion. A model is then derived in the form of a transformation matrix to relate the fiducial system, being fiducial key 10 in one particular embodiment, to the coordinate system of the surgical site. The resulting virtual construct may be used by surgical procedure planning software for virtual modeling of the contemplated procedure, and may alternatively be used by instrumentation software for the configuration of the instrument, for providing imaging assistance for surgical software, and/or for plotting trajectories for the conduct of the surgical procedure.

In some embodiments, the monitoring hardware includes a tracking attachment to the fiducial reference. In the embodiment pertaining to dental surgery the tracking attachment to fiducial key 10 is tracking marker 12, which is attached to fiducial key 10 via tracking pole 11. Tracking marker 12 may have a particular identifying pattern. The trackable attachment, for example tracking marker 12, and even associated tracking pole 11 may have known configurations so that observational data from tracking pole 11 and/or tracking marker 12 may be precisely mapped to the coordinate system and thus progress of the surgical procedure may be monitored and recorded. For example, as particularly shown in FIG. 3J, fiducial key 10 may have hole 15 in a predetermined location specially adapted for engagement with insert 17 of tracking pole 11. In such an arrangement, for example, tracking poles 11 may be attached with a low force push into hole 15 of fiducial key 10, and an audible haptic notification may thus be given upon successful completion of the attachment.

It is further possible to reorient the tracking pole during a surgical procedure. Such reorientation may be in order to change the location of the procedure, for example where a dental surgery deals with teeth on the opposite side of the mouth, where a surgeon switches hands, and/or where a second surgeon performs a portion of the procedure. For example, the movement of the tracking pole may trigger a re-registration of the tracking pole with relation to the coordinate system, so that the locations may be accordingly adjusted. Such a re-registration may be automatically initiated when, for example in the case of the dental surgery embodiment, tracking pole 11 with its attached tracking marker 12 are removed from hole 15 of fiducial key 10 and another tracking marker with its associated tracking pole is connected to an alternative hole on fiducial key 10. Additionally, boundary conditions may be implemented in the software so that the user is notified when observational data approaches and/or enters the boundary areas.

The tracker of the system may comprise a single optical imager obtaining a two-dimensional image of the site being monitored. The system and method described in the present specification allow three-dimensional locations and orientations of tracking markers to be obtained using non-stereo-pair two-dimensional imagery. In some embodiments more than one imager may be employed as tracker, but the image information required and employed is nevertheless two-dimensional. Therefore the two imagers may merely be employed to secure different perspective views of the site, each imager rendering a two-dimensional image that is not part of a stereo pair. This does not exclude the employment of stereo-imagers in obtaining the image information about the site, but the system and method are not reliant on stereo imagery of the site.

In a further embodiment of the system utilizing the invention, a surgical instrument or implement, herein termed a "hand piece" (see FIGS. 5 and 6), may also have a particular configuration that may be located and tracked in the coordinate system and may have suitable tracking markers as described herein. A boundary condition may be set up to indicate a potential collision with virtual material, so that when the hand piece is sensed to approach the boundary condition an indication may appear on a screen, or an alarm sound. Further, target boundary conditions may be set up to indicate the desired surgical area, so that when the trajectory of the hand piece is trending outside the target area an indication may appear on screen or an alarm sound indicating that the hand piece is deviating from its desired path.

An alternative embodiment of some hardware components are shown in FIGS. 3G-I. Fiducial key 10' has connection elements with suitable connecting portions to allow a tracking pole 11' to position a tracking marker 12' relative to the surgical site. Conceptually, fiducial key 10' serves as an anchor for pole 11' and tracking marker 12' in much the same way as the earlier embodiment, although it has a distinct shape. The software of the monitoring system is pre-programmed with the configuration of each particularly identified fiducial key, tracking pole, and tracking marker, so that the location calculations are only changed according to the changed configuration parameters.

A further aspect of the invention relates to the mounting of fiducial key 10 and is described at the hand of FIG. 3K, showing a multipodal surgical screw fixture for fiducial key 10. This arrangement addresses dental surgery, though it is by no means limited to dental surgery applications. It is particularly useful in cases where a dental patient lacks teeth near the surgical site. In the dental surgery application, surgical screw 22 is used to fasten mount 23 of fiducial key 10 of FIGS. 3A, 3B, 3C, 3D, 3E, and 3J to the bone structure of the mandible or maxilla via hole 24. This may be viewed as an alternative mounting to that shown in FIGS. 3G, 3H, and 3I. Practitioners in the field will appreciate that such a mounting procedure presents some challenges in securing a desired and stable orientation for fiducial key 10 and any fiducial extensions or tracking poles and tracking markers that may be attached to it. To provide the mount of fiducial key 10 with more stability and adjustability, it is provided with three surgical nail legs 26, 27, and 28 arranged to engage with the gums covering the maxilla or mandible. Together with surgical screw 22, legs 26, 27, and 28 provide fiducial key 10 with a stable and adjustable tripod mount, allowing a method of stably and adjustably mounting fiducial key 10 multipodally proximate the surgical site. In other embodiments different numbers of nail legs may be employed, but they are a plurality in all embodiments. In general, fiducial key 10 or 10' is therefore attached multipodally to the bone structure of the patient proximate the surgical site by means of at least one surgical screw and a plurality of surgical nails.

In Figure K fiducial key 10 and mount 23 are shown as separate subassemblies, but in other embodiments mount 23 may be monolithically integrated with fiducial key 10 so that the fiducial key itself comprises the mount, the hole and the nails.

In a further aspect of the invention, FIGS. 3L, 3M, and 3N show three different embodiments of fiducial extensions, being extensions 18, 18' and 18" respectively, representing in conjunction with fiducial key 10 respectively fiducial references 20, 20' and 20". Fiducial extensions 18, 18' or 18" may respectively be rigidly but removably attached to fiducial key 10 using, by way of example, the same mechanism as employed to attach tracking pole 11 to fiducial key 10. That is, fiducial extensions 18, 18' and 18" may respectively comprise insert 19, 19', 19" of the same shape as insert 17 of tracking pole 11. This arrangement ensures that, even though fiducial extensions 18, 18' and 18" may easily be removably attached to fiducial key 10 of FIGS. 3A, 3B, 3C, 3D, 3E, and 3J by means of hole 15, the collective fiducial references 20, 20' and 20" that result from the combining of fiducial key 10 and fiducial extensions 18, 18' and 18" are rigid to a degree that allows all mutually relative three dimensional locations on the surface of each of fiducial references 20, 20' and 20" to be known to an accuracy suitable for use in surgical imaging. Fiducial extensions 18, 18' and 18" may be radio-opaque and thereby function without the need for radio-opaque markings. In other embodiments, fiducial extensions 18, 18', and 18" may be transparent to scan radiation and may bear a radio-opaque pattern to provide the required fiducial function.

Fiducial extensions 18, 18' and 18" may comprise a three dimensional shape or markings that extend the radio-opaque fiducial shape or markings of fiducial key 10 beyond the physical confines of fiducial key 10. As a result, even though respective fiducial references 20, 20' and 20" are comprised of two components, being fiducial key 10 and respectively fiducial extensions 18, 18' and 18", each of these combinations 20, 20' and 20" nevertheless constitutes a single fiducial reference in operation within the monitoring system of the present invention. This stands in contrast to prior art fiducial arrangements based on the mutually independent placement of a plurality of individual point fiducials that are typically located relative to one another subsequent to placement.

As the arrangement of any of fiducial references 20, 20' and 20" extends further in three dimensions than that of fiducial key 10, it allows the three-dimensional location and orientation of respective fiducial reference 20, 20' or 20" to be determined with greater accuracy. Since the relative three-dimensional positions of locations on fiducial reference 20, 20' or 20" are pre-known with great accuracy, the image of fiducial reference 20, 20' or 20" in the scan data allows the system of the present invention to detect with good accuracy distortions that may occur in the scanning process. Such distortions are well known to practitioners in the field. In use, the scan data may simply be modified by processor 214 of computer system 210 (see FIG. 2) to adjust the location information of the fiducial reference 20, 20' or 20" in the scan data. The same correction may be extended to the entire scan.

Fiducial extension 18 of FIG. 3L represents the simple case of fiducial key 10 and the pattern on it being effectively extended in length to produce a larger distance over which to spatially calibrate scan data. This provides greater accuracy in spatially calibrating the scan data to the known exact dimensions of fiducial reference 20, and also provides greater scope for detecting spatial distortions in the scan data. In FIG. 3L the pattern is shown as repeating the same symbol, but, in a more general embodiment, any other usefully identifiable symbols may be employed in the extended pattern.

FIG. 3M shows fiducial extension 18' as a three-dimensionally shaped extension that makes the three-dimensional shape of fiducial reference 20' substantially different from that of fiducial key 10. That is, fiducial extension 18' is not only an extension of fiducial key 10, or of a pattern on fiducial key 10, but comprises portions that extend along directions that are non-parallel to any side or edge of fiducial key 10. While pattern symbols are shown on fiducial extension 18', but, in alternative embodiments, fiducial extension 18' may be opaque to scan radiation and may itself provide the required fiducial function, rather than being reliant on a radio-opaque marking for the fiducial function.

FIG. 3N shows fiducial extension 18" as a multi-pronged three-dimensionally shaped extension that makes the three-dimensional shape of fiducial reference 20" substantially different from that of fiducial key 10. That is, fiducial extension 18" is not only an extension of fiducial key 10, or of a pattern on fiducial key 10, but comprises multiple portions that extend along directions that are non-parallel to any side or edge of fiducial key 10. Pattern symbols are shown on a portion of fiducial extension 18". The pronged portions of fiducial extension 18" is shown as having no markings and may themselves be made of radio-opaque material so as to provide a fiducial function in a scan. In other embodiments, all of fiducial extension 18" may be substantially transparent to scan radiation and may bear suitably radio-opaque fiducial markings to produce a fiducial function in a scan.

In yet further embodiments, tracking pole 11 of FIGS. 3A, 3B, 3C, 3D, 3E and 3J or tracking pole 11' of FIGS. 3G, 3H, and 3I may be employed as fiducial extension in the same fashion as fiducial extensions 18, 18' and 18". To this end tracking pole 11 or 11' may either have a distinctive shape and be made from radio-opaque material, or it may be made from materials substantially transparent to scan radiation and bear upon its surface markings composed of radio-opaque materials.

In yet further embodiments, tracking marker 12 of FIGS. 3A, 3B, and 3F, or tracking marker 12' of FIGS. 3G and 3I may be employed additionally as fiducial extension to fiducial keys 10 or 10' respectively. To this end tracking marker 12 or 12' may either be made from radio-opaque material, or it may be made from materials substantially transparent to scan radiation and the markings it bears upon its surface may instead be composed of suitable radio-opaque materials. In some embodiments the markings on the surface of tracking marker may serve a dual function as both fiducial markings and tracking markings. In other embodiments, the tracking markings and fiducial markings may be different markings.

In yet further embodiments, tracking markers 12 or 12' may serve a dual function as both tracking markers and fiducial extensions as described above, but suitably distinctively shaped fiducial markers may be embedded within the tracking markers 12 or 12' while tracking markings are present on the surfaces of tracking markers 12 or 12'.

The materials of the hardware components may vary according to regulatory requirements and practical considerations. Generally, the key or fiducial component is made of generally radio-opaque material such that it does not produce noise for the scan, yet creates recognizable contrast on the scanned image so that any identifying pattern associated with it may be recognized. In addition, because it is generally located on the patient, the material should be lightweight and suitable for connection to an apparatus on the patient. For example, in the dental surgery example, the materials of the fiducial key must be suitable for connection to a plastic splint and suitable for connection to a tracking pole. In the surgical example the materials of the fiducial key may be suitable for attachment to the skin or other particular tissue of a patient.

The tracking markers are clearly identified by employing, for example without limitation, high contrast pattern engraving. The materials of the tracking markers are chosen to be capable of resisting damage in autoclave processes and are compatible with rigid, repeatable, and quick connection to a connector structure. The tracking markers and associated tracking poles have the ability to be accommodated at different locations for different surgery locations, and, like the fiducial keys, they should also be relatively lightweight as they will often be resting on or against the patient. The tracking poles must similarly be compatible with autoclave processes and have connectors of a form shared among tracking poles.

The tracker employed in tracking the fiducial keys, tracking poles and tracking markers should be capable of tracking with suitable accuracy objects of a size of the order of 1.5 square centimeters. The tracker may be, by way of example without limitation, a stereo camera or stereo camera pair.

While the tracker is generally connected by wire to a computing device to read the sensory input, it may optionally have wireless connectivity to transmit the sensory data to a computing device. In other embodiments, the tracker may be a non-stereo optical tracker.

In embodiments that additionally employ a trackable piece of instrumentation, such as a hand piece, tracking markers attached to such a trackable piece of instrumentation may also be light-weight; capable of operating in a 3-object array with 90 degrees relationship; optionally having a high contrast pattern engraving and a rigid, quick mounting mechanism to a standard hand piece.

Figure 4A:
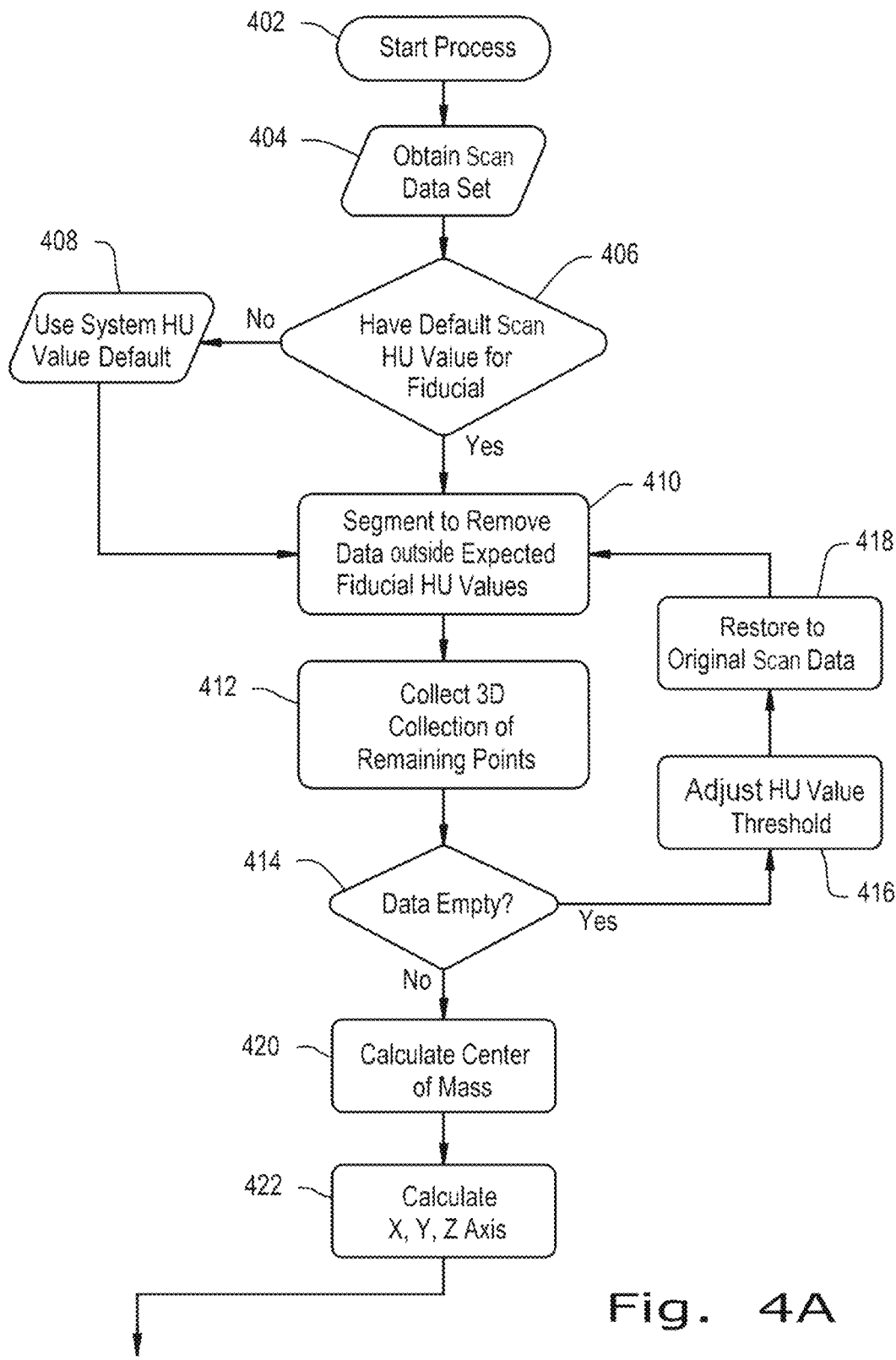
FIGS. 4A-D are flow chart diagrams illustrating one embodiment of the registering method of the present invention.
Figure 4B:
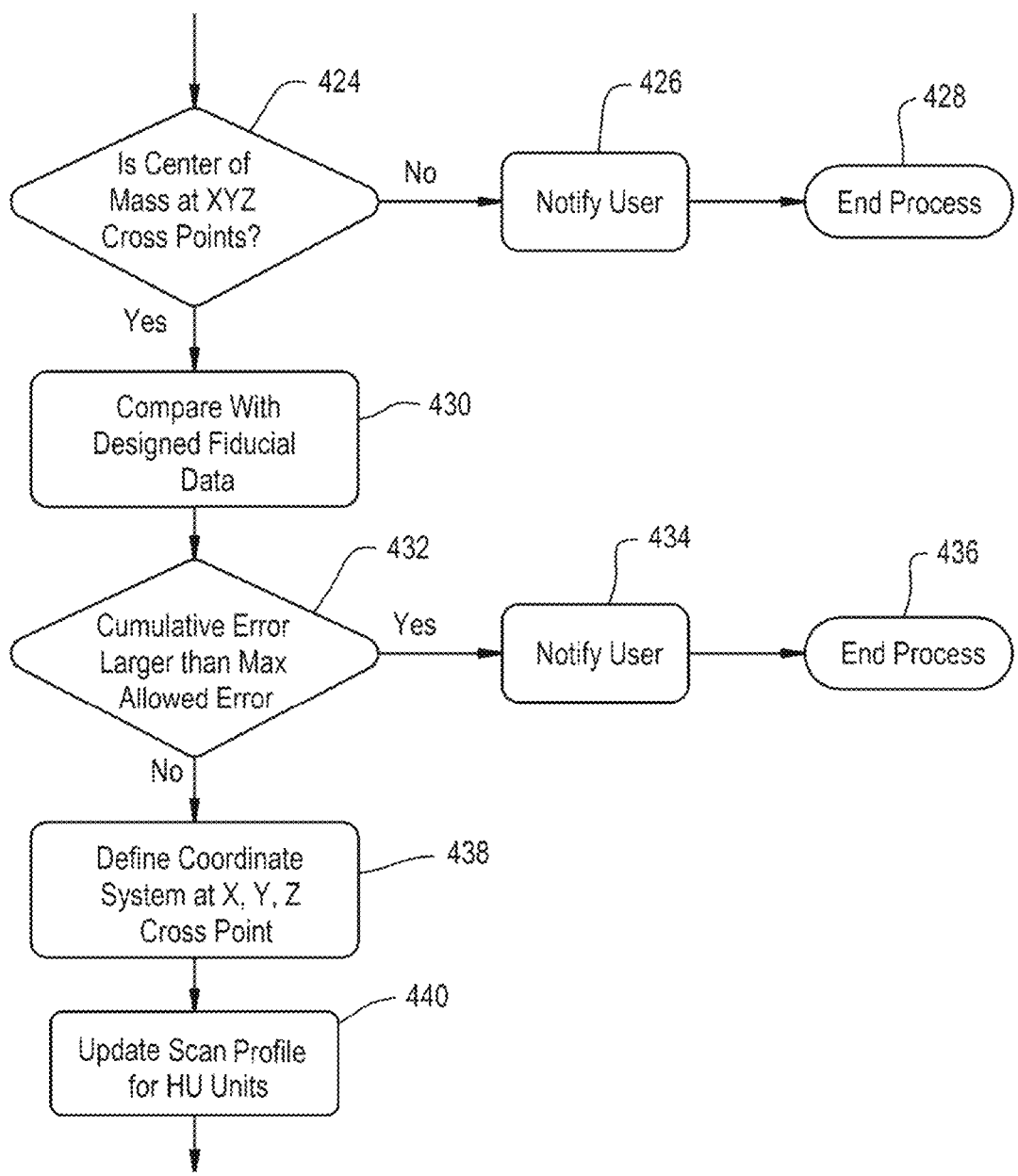
Figure 4C:
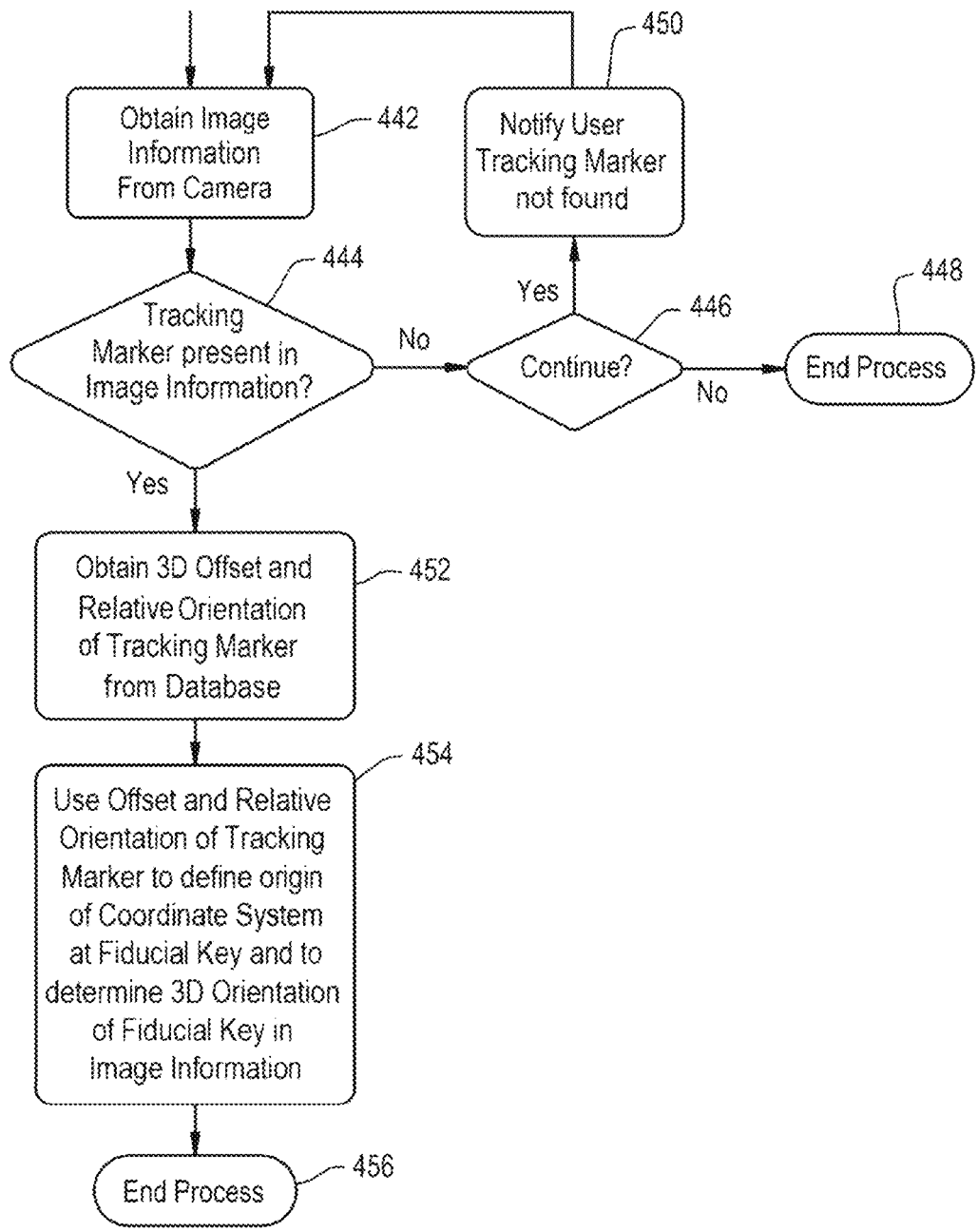

In another aspect there is presented an automatic registration method for tracking surgical activity, as illustrated in FIGS. 4A-C. FIG. 4A and FIG. 4B together present, without limitation, a flowchart of one method for determining the three-dimensional location and orientation of the fiducial reference from scan data. FIG. 4C presents a a flow chart of a method for confirming the presence of a suitable tracking marker in image information obtained by the tracker and determining the three-dimensional location and orientation of the fiducial reference based on the image information.

Once the process starts [402], as described in FIGS. 4A and 4B, the system obtains [404] a scan data set from, for example, a CT scanner and checks [at 406] for a default CT scan Hounsfield unit (HU) value for the fiducial which may or may not have been provided with the scan based on a knowledge of the fiducial and the particular scanner model, and if such a threshold value is not present, then a generalized predetermined default value is employed [408]. Next the data is processed by removing [at 410] scan segments with Hounsfield data values outside expected values associated with the fiducial key values, following the collection [at 412] of the remaining points. If the data is empty [at 414], the CT value threshold is adjusted [at 416], the original value restored [at 418], and the segmenting processing scan segments continues [at 410]. Otherwise, with the existing data a center of mass is calculated [at 420], along with calculating [at 422] the X, Y, and Z axes. If the center of mass is not at the cross point of the XYZ axes [at 424], then the user is notified [at 426] and the process stopped [at 428]. If the center of mass is at the XYZ cross point then the data points are compared [430] with the designed fiducial data. If the cumulative error is larger than the maximum allowed error [at 432] then the user is notified [at 434] and the process ends [at 436]. If not, then the coordinate system is defined [at 438] at the XYZ cross point, and the scan profile is updated for the HU units [at 440].

Turning now to FIG. 4C, image information is obtained [442] from the tracker, being a suitable camera or other sensor. The image information is two-dimensional and is not required to be a stereo image pair. The image information may be sourced from a single imaging device in the tracker, or may be sourced from multiple imaging devices in the tracker. It bears pointing out that the presence of multiple imaging devices in a tracker does not automatically imply stereo imaging. The image information is analyzed to determine [444] whether a tracking marker is present in the image information. If not, then the user is queried [446] as to whether the process should continue or not. If not, then the process is ended [448]. If the process is to continue, then the user may be notified [450] that no tracking marker has been found in the image information, and the process returns to obtaining image information [442]. If a tracking marker has been found based on the image information, or one has been attached by the user upon the above notification [at 450], the offset and relative orientation of the tracking marker to the fiducial reference is obtained [452] from a suitable database. The term "database" is used in this specification to describe any source, amount or arrangement of such information, whether organized into a formal multi-element or multi-dimensional database or not. A single data set comprising offset value and relative orientation may suffice in a simple implementation of this embodiment of the invention and may be provided, for example, by the user or may be within a memory unit of the controller or in a separate database or memory.

The offset and relative orientation of the tracking marker is used to define the origin of a coordinate system at the fiducial reference and to determine [454] the three-dimensional orientation of the fiducial reference based on the image information and the registration process ends [456]. In order to monitor the location and orientation of the fiducial reference in real time, the process may be looped back from step [454] to obtain new image information from the camera [at 442]. A suitable query point may be included to allow the user to terminate the process. Detailed methods for determining orientations and locations of predetermined shapes or marked tracking markers from image data are known to practitioners of the art and will not be dwelt upon here. The coordinate system so derived is then used for tracking the motion of any items bearing tracking markers in the proximity of the surgical site. Other registration systems are also contemplated, for example using current other sensory data rather than the predetermined offset, or having a fiducial with a transmission capacity.

Figure 4D:
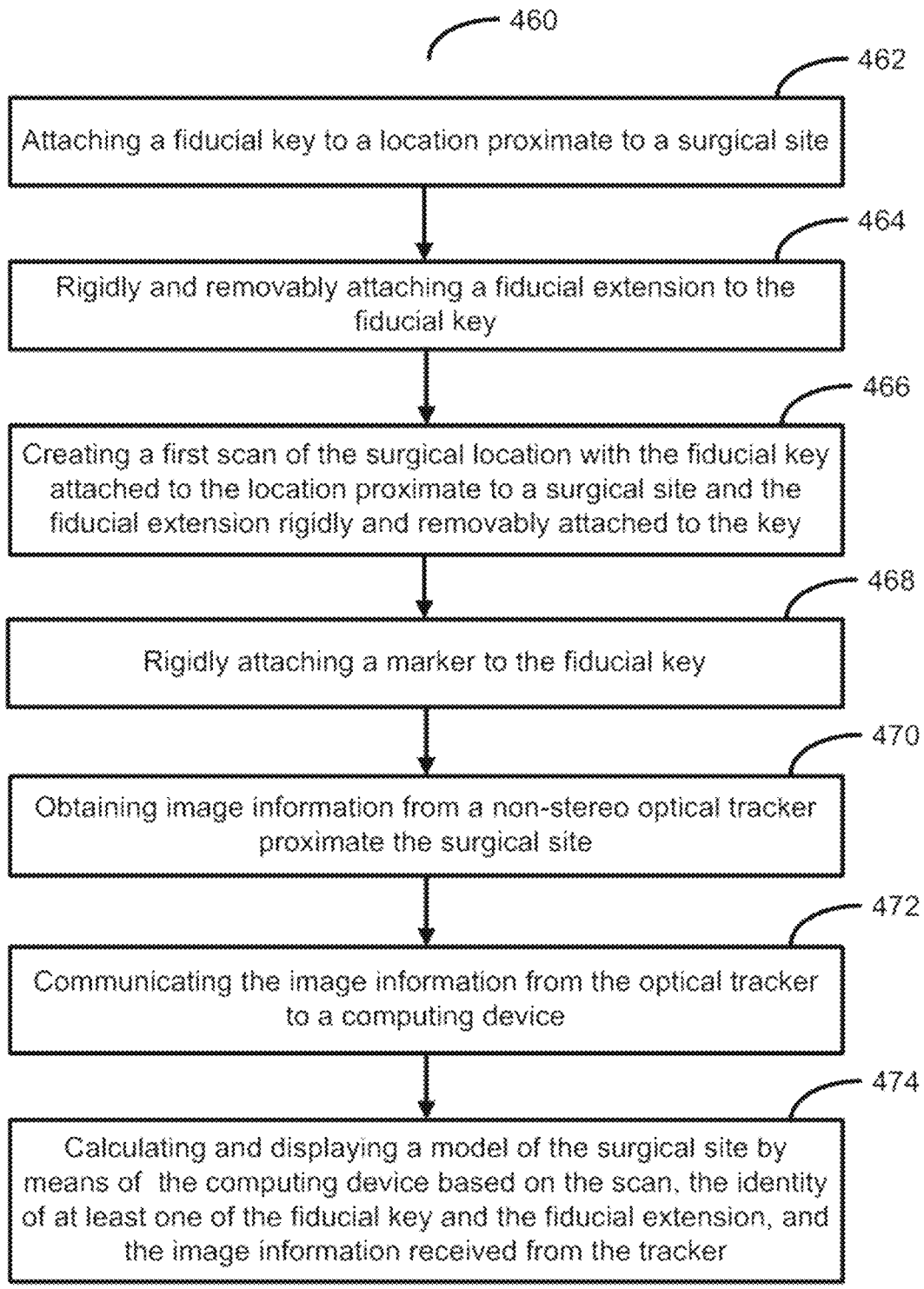

In a further aspect of the invention, shown in the flow chart of FIG. 4D, method [460] is provided for monitoring a surgical site, comprising: attaching [462] a fiducial key to a location proximate to a surgical site; rigidly and removably attaching [464] a fiducial extension to the fiducial key; creating [466] a first scan of the surgical location with the fiducial key attached to the location proximate to a surgical site and the fiducial extension rigidly and removably attached to the fiducial key; rigidly attaching [468] a marker to the fiducial key; obtaining [470] image information from a non-stereo optical tracker proximate the surgical site; communicating [472] the image information from the optical tracker to a computing device; and calculating [474] and displaying a model of the surgical site by means of the computing device based on the scan, the identity of at least one of the fiducial key and the fiducial extension, and the image information received from said tracker. The attaching [462] the fiducial key may comprise multipodally attaching the fiducial key by means of a surgical screw and a plurality of surgical nails.

Figure 5:
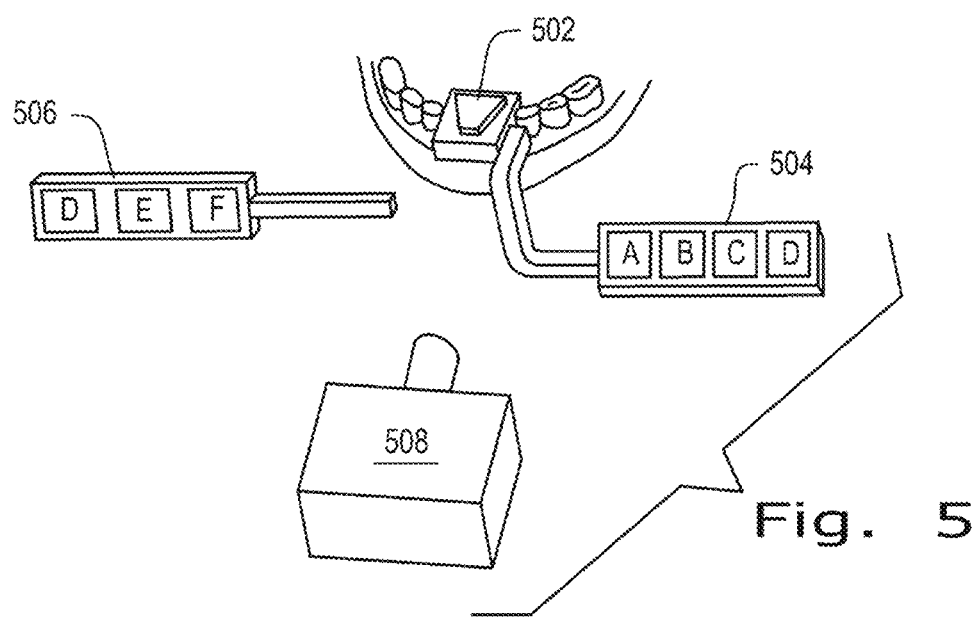
FIG. 5 is a drawing of a dental fiducial key with a tracking pole and a dental drill according to one embodiment of the present invention.
Figure 6:
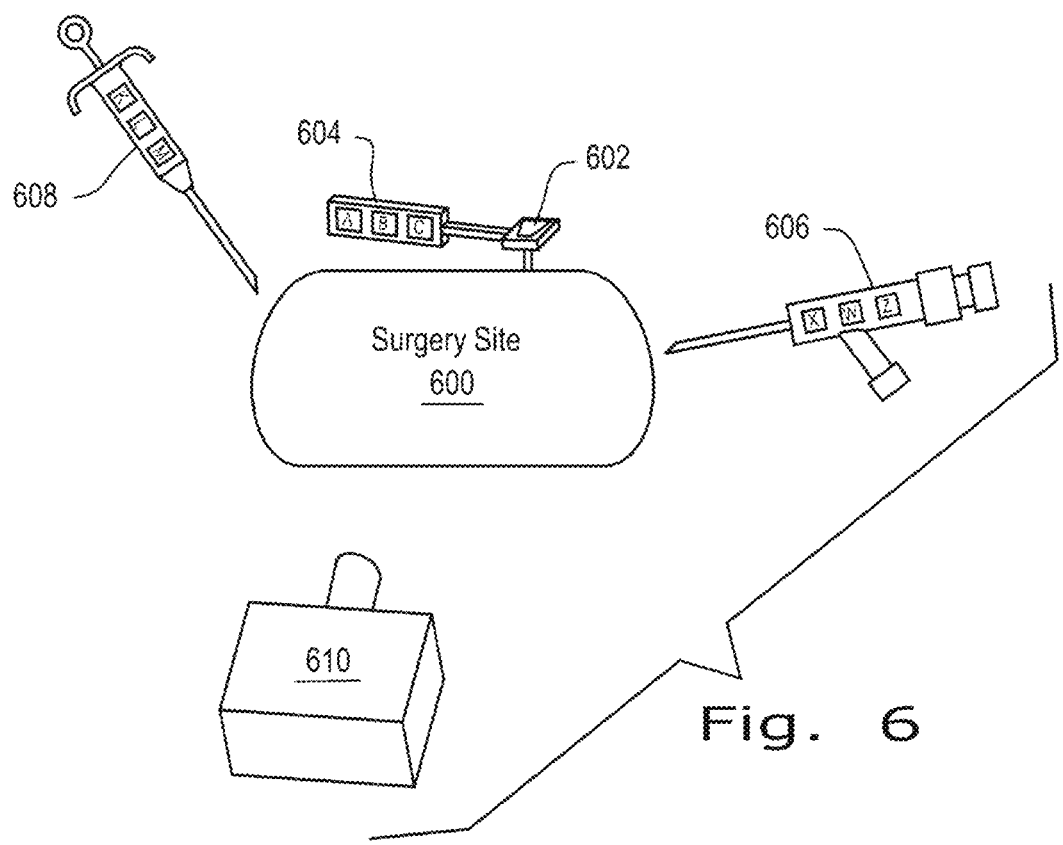
FIG. 6 is a drawing of an endoscopic surgical site showing the fiducial key, endoscope, and biopsy needle according to another embodiment of the invention.

One example of an embodiment of the invention is shown in FIG. 5. In addition to fiducial key 502 mounted at a predetermined tooth and having a rigidly mounted tracking marker 504, an additional instrument or implement 506, for example a hand piece which may be a dental drill, may be observed by a camera 508 serving as tracker of the monitoring system. The camera may be, for example, a non-stereo optical camera.

Another example of an embodiment of the invention is shown in FIG. 6. Surgery site 600, for example a human stomach or chest, may have fiducial key 602 fixed to a predetermined position to support tracking marker 604. Endoscope 606 may have further tracking markers, and biopsy needle 608 may also be present bearing a tracking marker at surgery site 600. Sensor 610, may be for example a camera, infrared sensing device, or RADAR. The camera may be, for example, a non-stereo optical camera.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A position monitoring system for a surgical procedure comprising:
   a single fiducial reference comprising a fiducial key and a fiducial extension rigidly and removably attached to the fiducial key, the fiducial key adapted to be fixed to an area of surgical patient;
   a first marker attached to the fiducial key in a predetermined fixed relative position and orientation;
   a non-stereo optical tracker able to determine the position and orientation of the first marker;
   a computer system having scan data of the patient with the fiducial reference fixed to the area of surgical patient, the computer system coupled to the tracker and including a processor with memory and a software program having a series of instructions which when executed by the processor determines the relative position and orientation of the first marker based on image information from the tracker, and relates the current position and orientation of the fiducial reference to the scan data; and
   a display system in communication with the computer system, the display system adapted to show the current position and orientation of the fiducial reference relative to the patient scan data during the surgical procedure.

2. The position monitoring system according to claim 1, wherein the fiducial key is fixed to the area of surgical patient such that the fiducial reference is at least partially non-visible during the surgical procedure.

3. The position monitoring system according to claim 1, wherein at least one of the fiducial key and the fiducial extension consists of a specific material that is distinctly identifiable in at least one of an X-ray image, Magnetic Resonance Image (MRI), computerized tomograph (CT), sonograph, and cone beam computerized tomograph (CBCT).

4. The position monitoring system according to claim 1, wherein at least one of the fiducial key and the fiducial extension has a distinct shape which allows its position and orientation to be determined from the scan data.

5. The position monitoring system according to claim 1, wherein at least one of the fiducial key and the fiducial extension has a label in a predetermined position such that the orientation of the fiducial reference is determined from the scan data.

6. The position monitoring system according to claim 1, wherein the fiducial key is configured and arranged to fit the part of the patient being scanned.

7. The position monitoring system according to claim 1, wherein the first marker has a distinct sensible characteristic which is identifiable in image information from the tracker.

8. The position monitoring system according to claim 1, wherein the first marker has a distinct shape such that the orientation of at least one of the fiducial key and the fiducial extension is determined from an image, or sequence of images, from the tracker.

9. The position monitoring system according to claim 1, wherein the first marker is identifiable as a specific code determinable from the image information.

10. The position monitoring system according to claim 9, wherein the specific code determines a specific marker whose position and orientation relative to at least one of the fiducial key and the fiducial extension is known and fixed.

11. The position monitoring system according to claim 1, wherein the first marker is adaptable in its physical arrangement to permit unobstructed access to an operation site during different procedures or stages of a procedure.

12. The position monitoring system according to claim 1, wherein the first marker is one of shaped or marked to be identifiable in the scan and the scan data comprises data of a scan obtained with the first marker attached to the fiducial key.

13. The position monitoring system according to claim 1, further comprising a mounting arrangement between the fiducial key and the first marker, the mounting arrangement arranged such that the first marker is removable such that a second marker is positionable in the mounting arrangement and the relative position of the first marker and the fiducial key is preserved.

14. The position monitoring system according to claim 1, further comprising a second marker, the second marker being attached to an implement such that the position and orientation of the second marker is determined by the software program.

15. The position monitoring system according to claim 14, wherein the position and orientation of the second marker is detected contemporaneously relative to at least one of the fiducial key and the fiducial extension.

16. The position monitoring system according to claim 14, further including a plurality of second markers and corresponding attached implements, wherein each of the plurality of second markers is individually distinct so that an identity of the corresponding attached implement is determinable from the image information.

17. The position monitoring system according to claim 16, wherein each of the attached implements has an operating point and the software program determines the position of the operating point relative to the patient scan data.

18. The position monitoring system according to claim 17, wherein the operating point includes one of a drill bit of a dental drill, a sensor of an endoscope, and a blade of a scalpel.

19. The position monitoring system according to claim 16, wherein one of the plurality of corresponding attached instruments has a plurality of distinct identifiable second markers attached to different parts of the one corresponding attached implement such that at least one of the plurality of distinct identifiable second markers is apparent to the tracker in any orientation of the one corresponding attached implement.

20. The position monitoring system according to claim 14, wherein the implement is one of a dental drill, an endoscope, a biopsy needle and a surgical implant.

21. The position monitoring system according to claim 1, further comprising a multipodal screw fixture for fixing the fiducial key to the area of the surgical patient.

22. The position monitoring system according to claim 21, wherein the multipodal screw fixture is monolithically integrated with the fiducial key.

23. The position monitoring system according to claim 1, wherein the first marker is attached to the fiducial key by a tracking pole.

24. The position monitoring system according to claim 23, wherein the fiducial extension comprises the tracking pole and the tracking pole is at least one of shaped and marked to be identifiable in the scan data.

25. A system for monitoring a surgical site, comprising:
a fiducial reference comprising a fiducial key and a fiducial extension rigidly and removably attached to the fiducial key, the fiducial key capable of attaching to a location proximate to a surgical site, at least one of the fiducial key and the fiducial extension having a marking perceptible on a scan;
a marker having a fixed connection with the at least one of the fiducial key and the fiducial extension;
a non-stereo optical tracker for observing the surgical site and transmitting image information of the surgical site; and
a computing device in communication with the tracker and having software capable of recognizing the at least one of the fiducial key and the fiducial extension and calculating a model of the surgical site based on the scan, the identity of the at least one of the fiducial key and the fiducial extension, and the image information received from the tracker.

26. The position monitoring system according to claim 25, wherein at least one of the fiducial key and the fiducial extension are adapted to be attached to an area of surgical patient that is at least partially internal.

27. The position monitoring system according to claim 26, further comprising a multipodal screw fixture for fixing the fiducial key to the location proximate to the surgical site.

28. The position monitoring system according to claim 27, wherein the multipodal screw fixture is monolithically integrated with the fiducial key.

29. A system for monitoring a surgical site, comprising:
a fiducial reference comprising a fiducial key and a fiducial extension rigidly and removably attached to the fiducial key, the fiducial key capable of attaching to an internal location proximate to a surgical site such that the at least one of the fiducial key and the fiducial extension is at least partially non-visible during the surgical procedure, the at least one of the fiducial key and the fiducial extension having a marking perceptible on a scan;
a marker having a fixed connection with the fiducial key;
an optical tracker for observing the surgical site and transmitting image information about the surgical site; and
a computing device in communication with the tracker and having a software program capable of recognizing at least one of the fiducial key and the fiducial extension and calculating a model of the surgical site based on the scan, the identity of the at least one of the fiducial key and the fiducial extension, and the image information received from the tracker.

30. The position monitoring system according to claim 29, further comprising a plurality of markers, and wherein the computing device includes a software program, each of the markers being attached to a corresponding implement such that the positions and orientations of the implements are determined by the software program.

31. The position monitoring system according to claim 30, wherein the position and orientation of the plurality of markers is detected contemporaneously relative to the at least one of the fiducial key and the fiducial extension.

32. The position monitoring system according to claim 30, wherein each of the plurality of markers is individually distinct so that an identity of the attached corresponding implement is determinable from the image information.

33. The position monitoring system according to claim 30, wherein each of the attached corresponding implements has an operating point and the computing device includes a software program that determines the position of the operating point relative to the patient scan data.

34. The position monitoring system according to claim 29, further comprising a multipodal screw fixture for attaching the fiducial key to the internal location proximate to the surgical site.

35. The position monitoring system according to claim 34, wherein the multipodal screw fixture is monolithically integrated with the fiducial key.

36. A system for monitoring a surgical site, comprising:
a single fiducial reference comprising a fiducial key and a fiducial extension rigidly and removably attached to the fiducial key, the fiducial key capable of attaching to a location proximate to a surgical site, at least one of the fiducial key and the fiducial extension having a marking perceptible on a scan;
a first marker having a fixed connection with the fiducial key;
an optical tracker for observing the surgical site and transmitting image information about the surgical site; and
a computing device in communication with the tracker and having a software program capable of recognizing the at least one of the fiducial key and the fiducial extension and calculating a model of the surgical site based on the scan, the identity of the at least one of the fiducial key and the fiducial extension, and the image information received from the tracker.

37. The position monitoring system according to claim 36, further comprising a plurality of second markers, each of the second markers being attached to a corresponding implement such that the positions and orientations of the implements are determined by the software program.

38. The position monitoring system according to claim 37, wherein the position and orientation of the plurality of second markers is detected contemporaneously relative to the at least one of the fiducial key and the fiducial extension.

39. The position monitoring system according to claim 37, wherein each of the plurality of second markers is individually distinct so that an identity of the attached corresponding implement is determinable from the image information.

40. The position monitoring system according to claim 37, wherein each of the attached corresponding instruments has an operating point and the software program determines the position of the operating point relative to the patient scan data.

41. The position monitoring system according to claim 36, further comprising a multipodal screw fixture for attaching the fiducial key to the location proximate to the surgical site.

42. The position monitoring system according to claim 41, wherein the multipodal screw fixture is monolithically integrated with the fiducial key.

43. A position monitoring system for surgical procedures comprising:
a fiducial reference comprising a fiducial key and a fiducial extension rigidly and removably attached to the fiducial key, the fiducial key adapted to be fixed to an area of a surgical patient;
a first marker attached to the fiducial key in a predetermined orientation;

at least one second marker attached to at least one corresponding implement, a non-stereo optical tracker able to determine the positions and orientations of the first and at least one second marker;

a computer system having a scan of the patient with the fiducial key fixed to the area of the surgical patient, the computer system coupled to the tracker and including a processor with memory and a software program having a series of instructions which when executed by the processor determines the relative positions and orientations of the first marker and the at least one further marker based on image information from the tracker, and relates the current arrangement of the at least one implement in relation to the scan data; and a display system in communication with the computer system, the display system adapted to show a current spatial arrangement of the at least one implement relative to the patient scan data during the surgical procedure.

44. The position monitoring system according to claim 43, further comprising a multipodal screw fixture for attaching the fiducial key to the area of the surgical patient.

45. The position monitoring system according to claim 44, wherein the multipodal screw fixture is monolithically integrated with the fiducial key.

46. A method for monitoring a surgical site, comprising:

attaching a fiducial key to a location proximate to a surgical site;

rigidly and removably attaching a fiducial extension to the fiducial key;

creating a first scan of the surgical location with the fiducial key attached to the location proximate to a surgical site and the fiducial extension rigidly and removably attached to the fiducial key;

obtaining image information from a non-stereo optical tracker proximate the surgical site;

communicating the image information from the optical tracker to a computing device; and calculating and displaying a model of the surgical site by means of the computing device based on the scan, the identity of at least one of the fiducial key and the fiducial extension, and the image information received from said tracker.

47. The method of claim 46, wherein the attaching the fiducial key comprises multipodally attaching the fiducial key by means of a surgical screw and a plurality of surgical nails.

* * * * *